(12) United States Patent
Godara et al.

(10) Patent No.: US 10,729,490 B2
(45) Date of Patent: Aug. 4, 2020

(54) ELECTROSURGICAL MAPPING TOOLS AND METHODS

(71) Applicant: Medtronic Holding Company Sàrl, Tolochenaz (CH)

(72) Inventors: Neil Godara, Milton (CA); Jason Woo, Mississauga (CA); Terence Cheong, Mississauga (CA)

(73) Assignee: Medtronic Holding Company Sàrl, Tolochenaz (CH)

( * ) Notice: Subject to any disclaimer, the term of this patent is extended or adjusted under 35 U.S.C. 154(b) by 679 days.

(21) Appl. No.: 14/852,761

(22) Filed: Sep. 14, 2015

(65) Prior Publication Data
US 2015/0374432 A1    Dec. 31, 2015

Related U.S. Application Data

(63) Continuation-in-part of application No. PCT/IB2014/059846, filed on Mar. 14, 2014.
(Continued)

(51) Int. Cl.
*A61B 18/14* (2006.01)
*A61B 17/34* (2006.01)
(Continued)

(52) U.S. Cl.
CPC ...... *A61B 18/1477* (2013.01); *A61B 17/3472* (2013.01); *A61B 18/148* (2013.01);
(Continued)

(58) Field of Classification Search
CPC .............. A61B 2034/107; A61B 34/20; A61B 2090/374; A61B 2090/3764;
(Continued)

(56) References Cited

U.S. PATENT DOCUMENTS 4,696,308 A * 9/1987 Meller ................ A61B 10/025
408/204
5,810,806 A * 9/1998 Ritchart ............. A61B 10/0266
604/21
(Continued)

FOREIGN PATENT DOCUMENTS

CN     201 194 837 Y    2/2009

OTHER PUBLICATIONS

European Search Report for EP 14 76 4517 the counterpart application dated Sep. 13, 2016, two pages.
(Continued)

*Primary Examiner* — Ronald Hupczey, Jr.

(57) ABSTRACT

A method and apparatus for treating tissue are disclosed, including intra-operative mapping of a probe ablation zone. The method uses a system that maps the proximal and distal margins of the probe ablation zone using tools that access the ablation target. In some embodiments, the tools comprise a bone drill, and an introducer assembly, including a cannula and a stylet. The tools have features or markings that cooperate to indicate which probe to use to achieve the desired ablation. The method further facilitates planning probe placement for delivering energy to treat (ablate) a desired ablation volume of a target tissue by using a system that maps both the target tissue and possible probe ablation zones.

20 Claims, 17 Drawing Sheets

Related U.S. Application Data

(60) Provisional application No. 61/786,986, filed on Mar. 15, 2013.

(51) Int. Cl.
  *A61B 18/00* (2006.01)
  *A61B 90/00* (2016.01)
  *A61B 17/16* (2006.01)

(52) U.S. Cl.
  CPC ...... *A61B 17/16* (2013.01); *A61B 2018/00208* (2013.01); *A61B 2018/00339* (2013.01); *A61B 2018/00565* (2013.01); *A61B 2018/00577* (2013.01); *A61B 2018/00702* (2013.01); *A61B 2018/00714* (2013.01); *A61B 2090/062* (2016.02); *A61B 2090/0811* (2016.02); *A61B 2090/376* (2016.02); *A61B 2090/3762* (2016.02); *A61B 2090/3937* (2016.02); *A61B 2090/3966* (2016.02)

(58) Field of Classification Search
  CPC ...... A61B 2090/376; A61B 2090/3762; A61B 2090/378; A61B 2090/3916; A61B 2090/392; A61B 2090/3925; A61B 2090/3929; A61B 2090/3954; A61B 2090/3966; A61B 2090/3983
  See application file for complete search history.

(56) References Cited

U.S. PATENT DOCUMENTS

| | | | |
|---|---|---|---|
| 6,451,015 B1* | 9/2002 | Rittman, III | A61B 18/1206 600/523 |
| 6,471,700 B1 | 10/2002 | Burbank et al. | |
| 6,478,793 B1* | 11/2002 | Cosman | A61B 18/1477 128/898 |
| 6,511,418 B2 | 1/2003 | Shahidi et al. | |
| 8,690,868 B2* | 4/2014 | Moorman | A61B 10/0233 601/101 |
| 2005/0038422 A1 | 2/2005 | Maurice | |
| 2005/0177209 A1 | 8/2005 | Leung et al. | |
| 2006/0079867 A1 | 4/2006 | Berzak et al. | |
| 2007/0161977 A1 | 7/2007 | Moorman et al. | |
| 2011/0137156 A1 | 6/2011 | Razzaque et al. | |
| 2012/0004594 A1 | 1/2012 | Schulz et al. | |
| 2012/0065495 A1 | 3/2012 | Richards-Kortum et al. | |
| 2012/0310230 A1* | 12/2012 | Willis | A61N 1/327 606/33 |

OTHER PUBLICATIONS

Examination Report and Search Report dated Oct. 4, 2019 from corresponding Canadian Application No. 2,906,286.
International Preliminary Report on Patentability dated Sep. 15, 2015 from International Application No. PCT/IB2014/059846.
Office Action dated May 28, 2020 in corresponding Canadian Patent Application No. 2,906,286.

\* cited by examiner

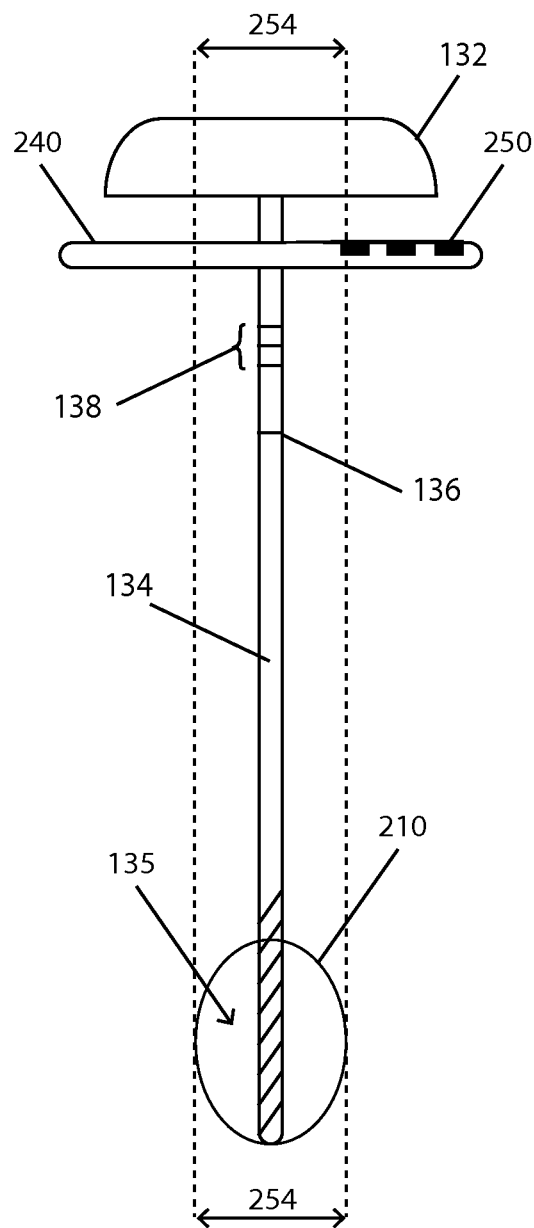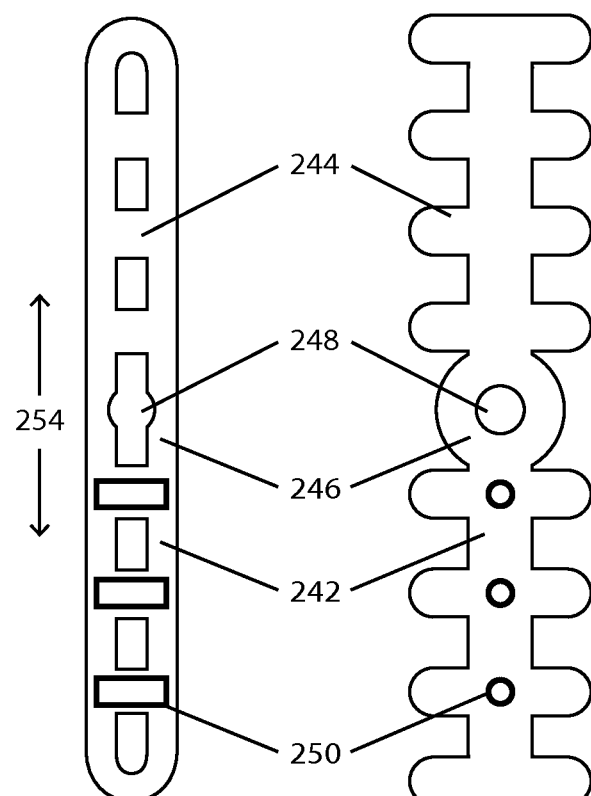
Fig. 12a
Fig. 12b  Fig. 12c

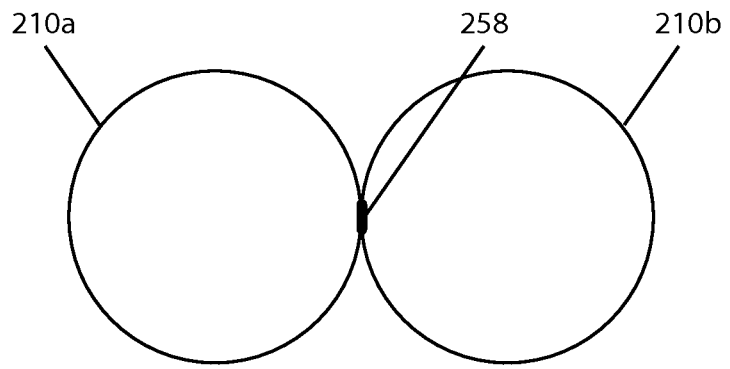
Fig. 12d (i)
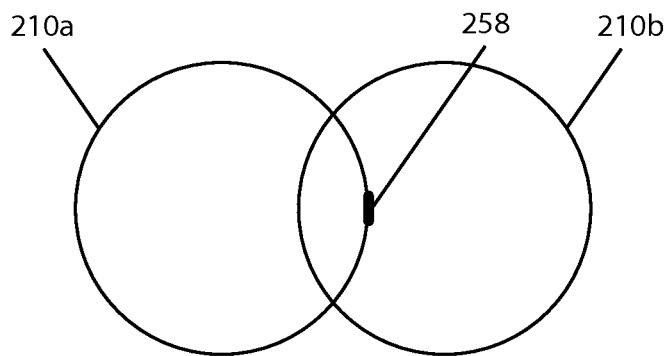
Fig. 12d (ii)
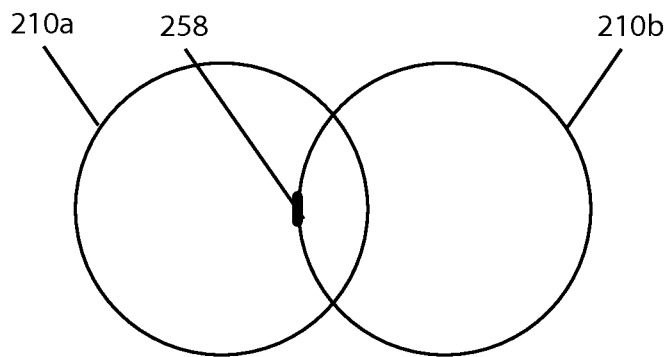
Fig. 12d (iii)

| Probe Group \ Active Tip | B | Y | G |
|---|---|---|---|
| PG 1 (100) | P1 | P2 | P3 |
| PG 2 (120) | P4 | P5 | P6 |
| PG 3 (140) | P7 | P8 | P9 |

Fig. 14 D

ELECTROSURGICAL MAPPING TOOLS AND METHODS

CROSS-REFERENCES TO RELATED APPLICATIONS

This application is a continuation-in-part of international application PCT/IB2014/059846, filed 14 Mar. 2014, which claims the benefit of U.S. provisional application 61/786,986, filed 15 Mar. 2103. Both of the aforementioned applications are hereby incorporated by reference in their entirety. Co-pending U.S. application Ser. No. 13/660,353, filed Oct. 25, 2012, and Ser. No. 13/643,310, filed Oct. 25, 2012 are hereby incorporated by reference in their entirety.

TECHNICAL FIELD

The disclosure relates to an electrosurgical device. More specifically, the disclosure relates to an electrosurgical probe and associated apparatus, and methods of use thereof.

SUMMARY OF THE DISCLOSURE

The present inventors have discovered and reduced to practice various embodiments of an apparatus for accessing and treating tissue by delivering energy that may be used with an imaging system to provide intra-operative mappings. The system provides intra-operative mappings of the probe ablation zones of different probes relative to an imaged target tissue. The mappings provide increased certainty of ablation boundaries, increased convenience in probe selection, and allow the user greater foresight in planning probe selection and placement.

In one broad aspect, embodiments of the present invention comprise a method for intra-operative mapping of a probe ablation zone. The method comprises accessing a treatment site using one or more treatment access tools, and defining and visualizing a proximal margin and a distal margin of a probe ablation zone using the one or more treatment access tools.

In another broad aspect, alternate embodiments of a method for intra-operative mapping of a probe ablation zone comprise accessing a treatment site using one or more treatment access tools; defining a proximal margin and a distal margin of a probe ablation zone using the one or more treatment access tools, the probe ablation zone being substantially equivalent to a target tissue being targeted for ablation; and selecting a probe using the one or more treatment access tools, the probe being operable to ablate a region of tissue larger than the probe ablation zone.

In a further broad aspect, embodiments of the present invention comprise a system for treating tissue including intra-operatively mapping a probe ablation zone. The system comprises an introducer assembly comprising a cannula and a stylet, the cannula defining a lumen and the stylet configured to fit within the lumen; a medical instrument for accessing tissue at a treatment site through the lumen of the cannula, the medical instrument including one or more indicia for defining a probe ablation zone; and one or more probes, each probe corresponding to one of the indicia, each probe operable to ablate tissue within a respective probe ablation zone.

In a further broad aspect, alternate embodiments of a system for treating tissue comprise an introducer assembly comprising a cannula and a stylet, the cannula defining a lumen; a plurality of medical instruments for accessing tissue at a treatment site through the lumen of the cannula, each medical instrument defining one or more indicia, each indicia defining a probe ablation zone; and one or more probes, each corresponding to a single indicia of the medical instrument, and operable to ablate tissue within a respective probe ablation zone.

In another broad aspect, embodiments of the present invention comprise a method for intra-operative probe selection for ablation of tissue at a treatment site. The method comprises mapping a proximal margin and a distal margin of a desired probe ablation zone/volume at the treatment site using a plurality of tools having cooperating features that determine probe selection for ablating the desired volume. As a feature of this aspect, some embodiments include performing more than one ablation. Typical embodiments include performing ablations that are longitudinally aligned along a probe advancement path. In some embodiments having more than one ablation, the proximal ablation is performed first, while in alternative embodiments, the furthest distal ablation is performed first.

In yet another broad aspect, alternate embodiments of a method for intra-operative probe selection for ablation of tissue at a treatment site comprise mapping a proximal margin and a distal margin of a probe ablation zone at the treatment site using access tools having cooperating features that determine probe selection from a group of probes for achieving a desired ablation defined by the probe ablation zone.

In another broad aspect, embodiments of the present invention comprise a method of ablating a target tissue. The method comprises positioning an introducer assembly, including a cannula and a stylet positioned therethrough, within a target tissue, thereby defining a proximal margin of a probe ablation zone; imaging the proximal margin of the probe ablation zone to thereby map the proximal margin; removing the stylet from the cannula; inserting a bone drill into the cannula; and advancing the bone drill until a distal tip of the bone drill is at a distal edge of a desired ablation volume, the distal tip thereby defining a distal margin of a probe ablation zone.

In another broad aspect, embodiments of the present invention comprise a method for mapping side-by-side probe ablation zones. The method comprises positioning a medical instrument coupled to an imaging tool at a target site; defining a first lateral probe ablation zone of a probe at a first position by visualizing a pair of visualization elements of the imaging tool; repositioning the medical instrument laterally; and defining a second lateral probe ablation zone of the probe at a second position.

In yet another broad aspect, some embodiments of the present invention comprise a method for intra-operative selection of a probe temperature for ablation of tissue at a treatment site. The method comprises mapping a target tissue at a treatment site using an imaging system to define a probe ablation zone; and using access tools with cooperating features that determine, for a particular probe, a pre-defined probe temperature for achieving a desired ablation defined by the probe ablation zone.

In another broad aspect, some embodiments of the present invention comprise a method for intra-operative selection of a treatment plan to ablate a target tissue requiring one or more ablations. The method comprises mapping a target tissue at a treatment site using an imaging system to define a probe ablation zone, and using access tools having cooperating features to determine a treatment plan for achieving a desired ablation defined by the probe ablation zone.

BRIEF DESCRIPTION OF THE DRAWINGS

In order that the invention may be readily understood, embodiments of the invention are illustrated by way of examples in the accompanying drawings, in which:

FIGS. 8b to 8d illustrate alternative methods of treating the target tissue of FIG. 8a;

FIG. 9b illustrates a method of treating the target tissue of FIG. 9a;

FIGS. 10b to 10d illustrate alternative methods of treating the target tissue of FIG. 10a;

FIGS. 12a to 12c illustrate an embodiment with an imaging tool;

FIG. 12d illustrates an example of the use of the embodiment of FIGS. 12a to 12c;

FIGS. 14a to 14d illustrate an embodiment related to selecting probes from groups of probes;

DETAILED DESCRIPTION

Figure 1:
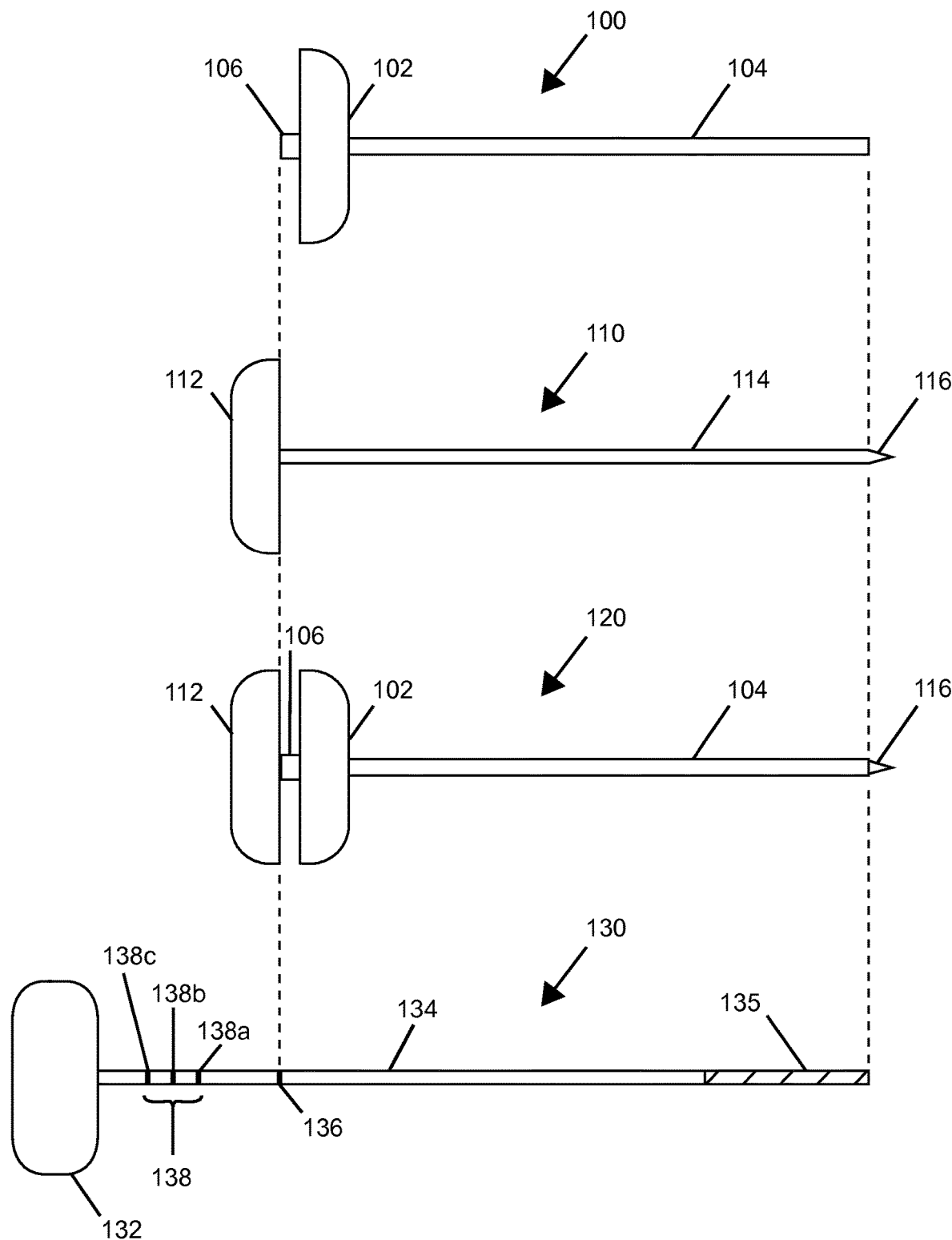
FIG. 1 is an illustration of an embodiment of the invention showing apparatus used for accessing a treatment site.

Procedures comprising the ablation of tissue typically require pre-operative imaging and mapping of the treatment site. For example, the ablation of spinal tumours requires a surgeon to pre-operatively map the size of the targeted tumor. As the tumor may grow between the time of imaging and the procedure, the surgeon must also estimate the expected growth rate of the tumor to predict its size on the procedure date, a task which may be challenging and potentially inaccurate. Furthermore, a surgeon may wish to plan an ablation procedure, including selecting probes and determining their position for one or more deliveries of energy. Computing such a plan is time consuming and often technically difficult.

The present inventors have discovered and reduced to practice various embodiments of an apparatus/system/kit for accessing and treating tissue by delivering energy that may be used with an imaging system to provide intra-operative mappings. The system provides intra-operative mappings of the probe ablation zones of different probes relative to an imaged target tissue. The mappings provide increased certainty of ablation boundaries, increased convenience in probe selection, and allow for greater foresight in planning probe selection and placement.

In particular, the inventors have conceived of tools used to gain access to a treatment site that have co-operating features which, under imaging, map the ablation zones of corresponding probes, facilitating the selection of probes for a desired ablation volume. In this description, the term "imaging" is used to describe the process of visualizing tissue as well as apparatus using an imaging system such as a fluoroscopic imaging system. The use of imaging coupled with the intra-operative delineation of the ablation zones using such access tools also supplies information about anatomy surrounding an ablation zone, which aids in avoiding the destruction of important body structures close to the target tissue. In some embodiments, a bone drill with markings/indicia is used with a cannula having a feature that cooperates with the drill markings to selectively position the distal tip of the bone drill to define and map the distal margin of a probe ablation zone. The particular bone drill marking or indicium chosen for mapping the ablation zone also identifies which probe should be used to produce the mapped ablation zone. In such embodiments, the cannula is part of an introducer assembly used in a method of defining a proximal margin of the probe ablation zone. Thus, the combination of the bone drill and introducer assembly functions to map, delineate, or define the proximal and distal margins of the ablation zone.

The selected marking or indicium on the bone drill may also identify other energy delivery parameters, such as time and probe temperature, that may be used to create a lesion corresponding to the probe ablation zone. The inventors have also discovered methods for positioning and re-positioning the access apparatus in situations when a desired ablation volume does not sufficiently correspond with the probe ablation zones of the available probes, and for situations requiring more than one delivery of energy.

While the above description includes using a bone drill, the invention is not limited to the above described apparatus. In some alternative embodiments for use in tissue that is not bone, such as soft tissue (i.e. tissue that is softer than bone), a needle for piercing tissue is used instead of a bone drill. For the purpose of this application, the term 'medical instrument' may refer to either a bone drill or a needle. Furthermore, embodiments comprising a bone drill may alternately comprise a needle, and embodiments comprising a needle may alternately comprise a bone drill.

Disclosed herein is a method for treating tissue including intra-operatively mapping a probe ablation zone, i.e., the extent to which a particular probe will ablate tissue in the probe's longitudinal direction. The method uses a system that maps the proximal and distal margins of the probe ablation zone with tools used to access the ablation target. In some embodiments, the tools comprise an introducer assembly, including a cannula and a stylet, and a bone drill. These tools are used with medical imaging systems for visualization purposes.

Further disclosed is a method for treating tissue, including intra-operative probe selection for ablation. The method comprises mapping a proximal margin and a distal margin of a probe ablation zone using tools with features or markings that cooperate to indicate the appropriate probe for achieving a particular ablation target or desired ablation volume. The method includes mapping at one or more locations. The method further facilitates probe placement for delivering energy to treat (ablate) a desired ablation volume of a target tissue by mapping both the target tissue and possible probe ablation zones.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Apparatus

FIGS. 1 to 5 illustrate embodiments of an apparatus used to perform methods of the invention. Some embodiments of the invention include a system for treating tissue comprising an introducer assembly including a cannula and a stylet (FIG. 2), an elongated medical instrument able to extend through the lumen and traverse a distance beyond the cannula (e.g. bone drill 130), and an imaging system (not shown in drawings). Disclosed methods include mapping a proximal margin of a probe ablation zone by positioning a distal tip of the introducer assembly to define the proximal margin and visualizing the positioned distal tip of the introducer assembly, and positioning a distal tip of the bone drill to define a distal margin of the probe ablation zone and visualizing the positioned distal tip of the medical instrument (bone drill) to map the distal margin of the probe ablation zone, to thereby map the probe ablation zone longitudinally. In some embodiments the imaging system is a fluoroscopic imaging system while in alternative embodiments it is a computed tomography (CT) imaging system.

Making reference to FIG. 1, an apparatus used for accessing a treatment site is illustrated, with the broken lines showing the corresponding lengths of the parts. In the embodiment of FIG. 1 introducer assembly 120 is comprised of cannula 100 and stylet 110. While the terms "stylet" and "cannula" may have different meanings in the medical art, for purposes of explanation, this disclosure will describe an introducer assembly as comprising a cannula and a stylet. Stylet 110 includes stylet handle 112, stylet shaft 114, and trocar tip 116. Stylet 110 fits inside cannula 100 and may be advanced or withdrawn therewithin. Cannula 100 includes cannula handle 102, cannula shaft 104, and hub 106. Hub 106 projects proximally from cannula handle 102, with handle 102 and hub 106 defining a longitudinal portion of the lumen, and the hub including the proximal end of cannula 100. When stylet 110 is inserted into cannula 100, trocar tip 116 extends beyond the distal end of cannula shaft 104, facilitating the advancement of introducer assembly 120 through tissue to a treatment site.

The embodiment of FIG. 1 includes an elongated medical instrument, bone drill 130, with markings thereupon. Bone drill 130 is comprised of bone drill handle 132, bone drill shaft 134, helical flutes 135 of drill shaft 134, cannula length marking 136 which indicates the cannula length, and probe selection markings 138 (i.e. indicia) which include markings 138a, 138b, and 138c. In alternative embodiments, the elongated medical instrument may be a needle for piercing tissue.

In general, cannula length marking 136 will cooperate with a feature of a cannula (i.e. a cooperating feature such as a window or slot in the cannula) to indicate that the distal end of bone drill 130 is at a distal end of the cannula. In the embodiment of FIG. 1, when bone drill 130 is inserted in cannula, cannula length marking 136 cooperates with the proximal end of cannula 100 to indicate to the user that the distal end of bone drill 130 is at a distal end of the cannula. The broken lines of FIG. 1 show that the length of bone drill shaft 134 is about equal to the length of the lumen of cannula 100.

In general, bone drill 130 (the medical instrument) has one or more indicia that correspond with one or more probes, with each of the probes operable to create an ablation zone having a unique length. Each indicium corresponds with a specific probe, and in some embodiments the indicia are color coded to correspond with color coded probes and/or a color coding system associated with the probes. The apparatus may further comprise packaging for the probes that includes the corresponding probe color codes. Bone drill 130 of FIG. 1 has three indicia comprising probe selection markings 138a, 138b, and 138c. In some embodiments, bone drill 130 has one indicium and is used with one probe. The methods described in this application may be used with such an embodiment, as appropriate.

Figure 2:
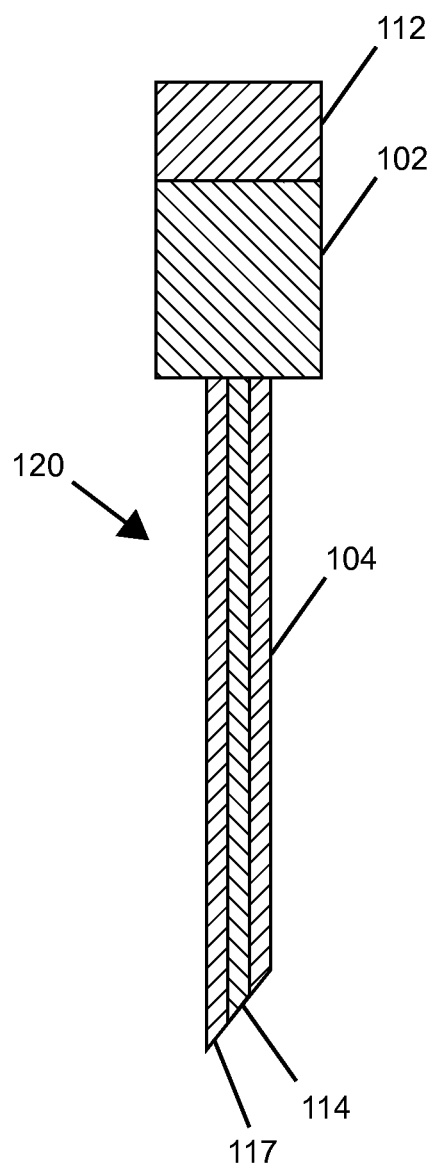
FIG. 2 is an illustration of an alternative embodiment of an introducer assembly.

FIG. 2 shows an alternative embodiment of introducer assembly 120 in which cannula shaft 104 has a sharp beveled tip 117. Cannula shaft 104 defines a lumen which stylet shaft 114 occludes to prevent coring of tissue. Introducer assembly 120 of FIG. 2 is typically used in tissue softer than bone.

Figure 3:
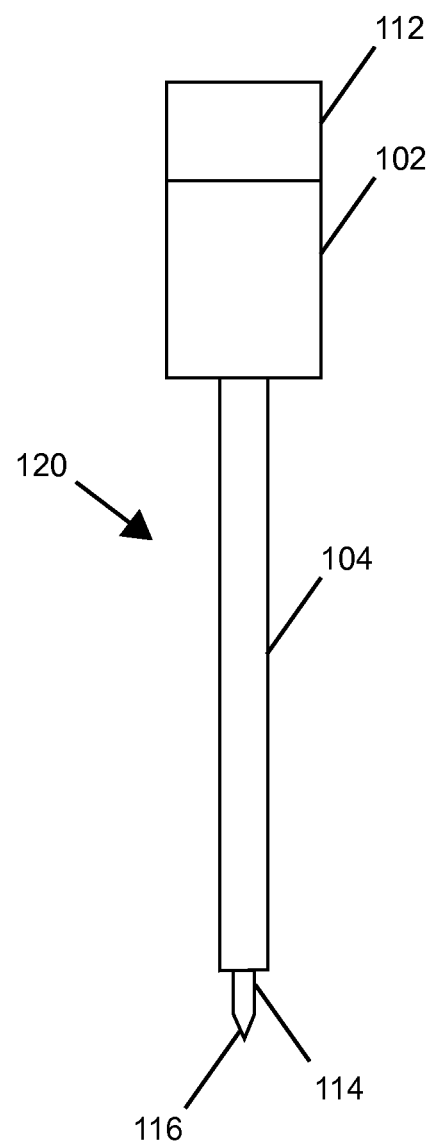
FIG. 3 is an illustration of another alternative embodiment of an introducer assembly.

FIG. 3 shows another alternative embodiment of introducer assembly 120 in which cannula shaft 104 has a blunt tip which is occluded by stylet shaft 114. A portion of stylet shaft, including trocar tip 116, extends beyond the distal end of cannula shaft 104. Typically, such an introducer assembly 120 may be used in bone.

Figure 4:
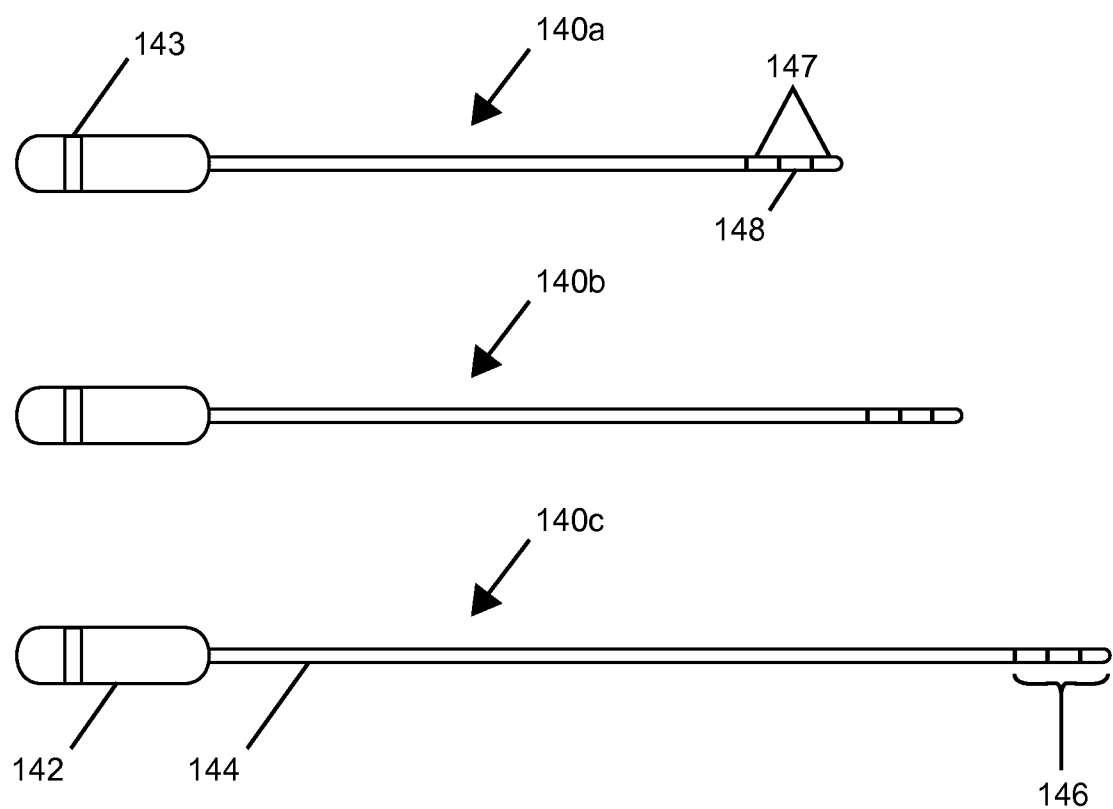
FIG. 4 is an illustration of a set of probes of an embodiment of the invention.

FIG. 4 illustrates of a set of probes for delivering electrical energy to tissue, including probes 140a, 140b and 140c. Each probe 140 is comprised of a probe handle 142, a probe identifier 143, a probe shaft 144, and an active tip 146 that includes at least one electrode 147 and at least one section of insulation 148. In the example of FIG. 4, an active tip comprises two electrodes 147 with insulation 148 between the electrodes. In some embodiments, the probes are operable to deliver energy in a bipolar manner. In the embodiment of FIG. 4, each of the probes has a unique active tip size (length) and would typically correspond with a unique probe ablation zone length. A probe with a longer active tip typically produces a larger lesion.

Embodiments of the invention typically include a generator for supplying electrical energy to the probes. In some embodiments, the electrical energy is in the radiofrequency range. In some embodiments, the generator supplies energy between about 1 watt and about 100 watts. In other embodiments, the generator supplies energy between about 1 watt and about 50 watts. In yet other embodiments, the generator supplies energy greater than about 100 watts or less than about 1 watt.

Some embodiments comprise a temperature look-up table for storing the operating temperatures of each probe 140. The look-up table may be stored in a generator, or alternatively, in another device. In some embodiments the operating temperature is referenced using the indicia (e.g. probe selection markings 138). The operating temperatures may be referenced using operating temperature color codes that also correspond with probe color codes. For example, some embodiments include generator switches for selecting probe operating temperatures that are color coded to correspond with probe color codes and/or indicia color codes.

In some examples, the system further comprises a generator that communicates with a connected probe, and the system is operable to detect a probe identifier and select a corresponding operating temperature from the temperature look-up table.

Figure 5:
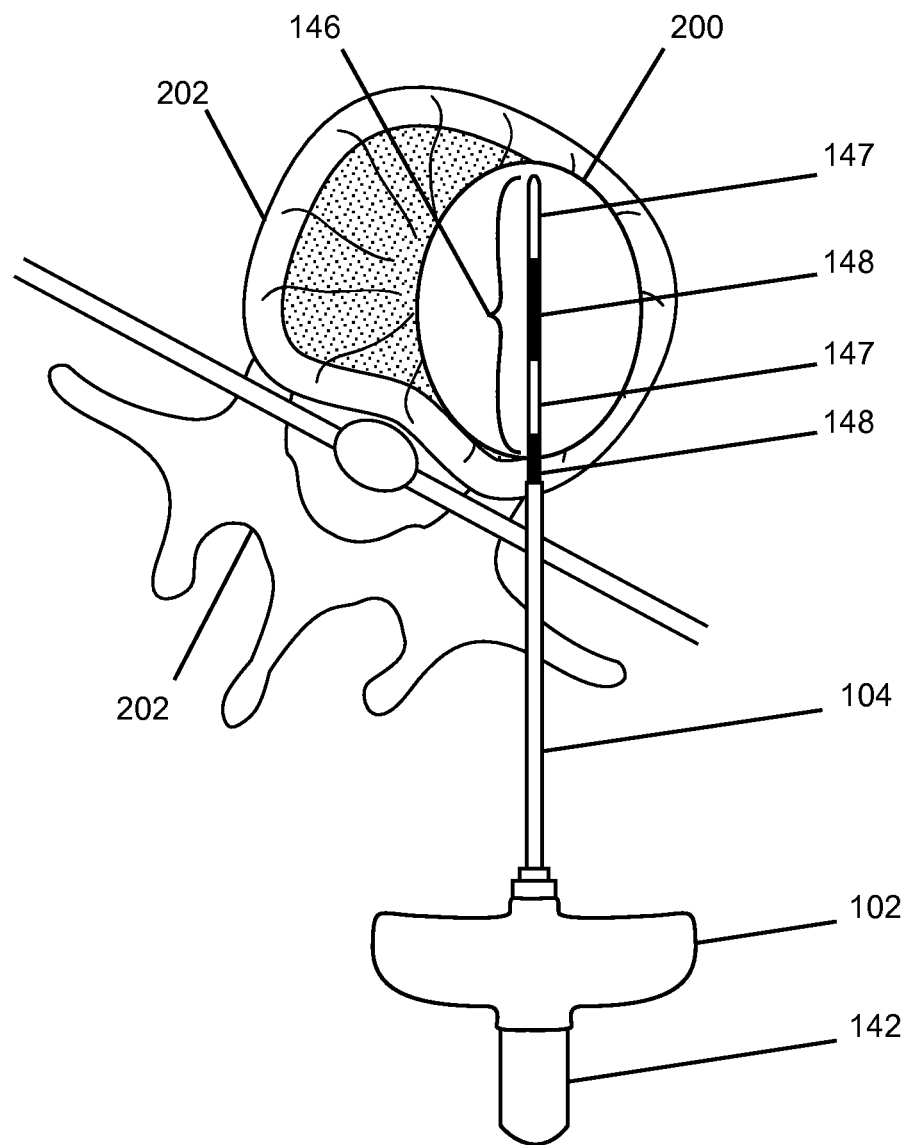
FIG. 5 is an illustration of the use of an embodiment of the invention for creating a lesion.

FIG. 5 illustrates a treatment site after the use of a probe 140. In this particular embodiment, the method includes inserting and advancing an introducer assembly 120 comprising a cannula 100 with a stylet 110 disposed therein to a location within a patient's body. In the example of FIG. 5, the target tissue 203 location is in a vertebral body or a bone 202. Once the user positions the introducer assembly 120 at the target site, he/she withdraws stylet 110 from cannula 100 and inserts a probe 140 through the cannula to the target site. The user then delivers energy (e.g. RF energy) to form a lesion 200 adjacent the active tip 146 within the vertebral body. In some embodiments energy is delivered in a bipolar manner between the two electrodes 147.

Details about probes that may be used in the disclosed methods are described in U.S. application Ser. Nos. 13/643,310 and 13/660,353, each incorporated by reference in its entirety.

Methods

FIGS. 6a to 6d illustrate a method of treating tissue for a case in which the target tissue 203 can be ablated with a single energy delivery. The method includes mapping a proximal margin 212 and a distal margin 214 of the probe ablation zone 210 using tools that provide access to the treatment site. The proximal margin 212 and distal margin 214 of the probe ablation zone 210 define the longitudinal boundaries of the area to be ablated.

Figure 6A:
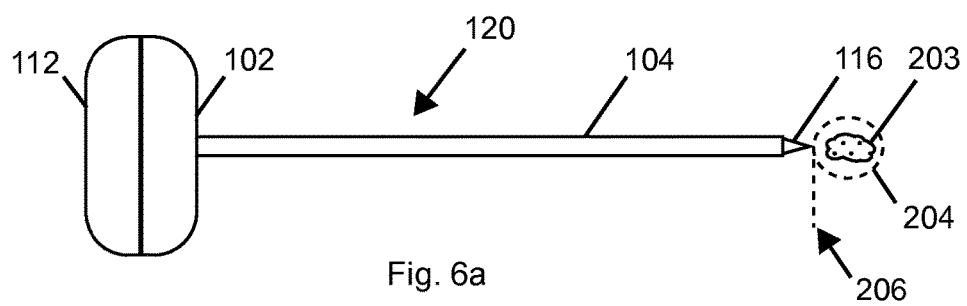
FIGS. 6a to 6d illustrate an embodiment of a method of the invention, including the ablation of a target tissue for a situation in which the target tissue can be ablated with a single energy delivery.

FIG. 6a illustrates introducer assembly 120 comprising cannula 100 containing stylet 110. The user has positioned the distal tip of introducer assembly 120 (trocar tip 116) at proximal edge 206 of desired ablation volume 204. The proximal margin 212 (FIG. 6c) of probe ablation zone 210 is defined by the position of distal tip of introducer assembly 120 and mapped by visualizing the distal tip of the introducer assembly. Note that the distal tip of introducer assembly 120 is not at the edge of target tissue 203. In the example of FIG. 6, proximal edge 206 of the desired ablation volume 204 and proximal margin 212 of probe ablation zone 210 are equivalent or coincident (i.e. they are both mapped by the distal tip of introducer assembly 120), but in other examples (described herein below) proximal edge 206 and proximal margin 212 are not equivalent. The desired ablation volume 204 of FIG. 6a includes some tissue surrounding target tissue 203. In some cases, for example, if target tissue 203 is a tumor, a physician would typically ablate some surrounding tissue to ensure the complete destruction of the target tissue.

Figure 6B:
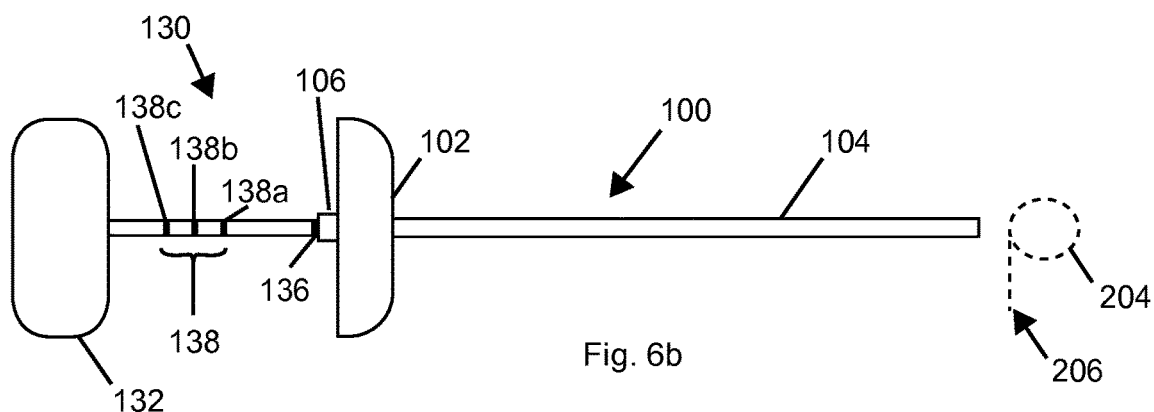

The method includes withdrawing stylet 110 and replacing it with a medical instrument such as a bone drill 130. FIG. 6b shows bone drill 130 after the user has advanced it through a lumen of cannula 100 such that a marking on bone drill 130 (cannula length marking 136) lines up with a feature of cannula 100 (the proximal end of hub 106) to indicate that the distal end of bone drill 130 is at the distal end of cannula 100. In this configuration, (after stylet 110 is withdrawn from cannula 100) there is a gap between the distal tip of cannula 100 and desired ablation volume 204, as shown in FIG. 6b.

Figure 6C:
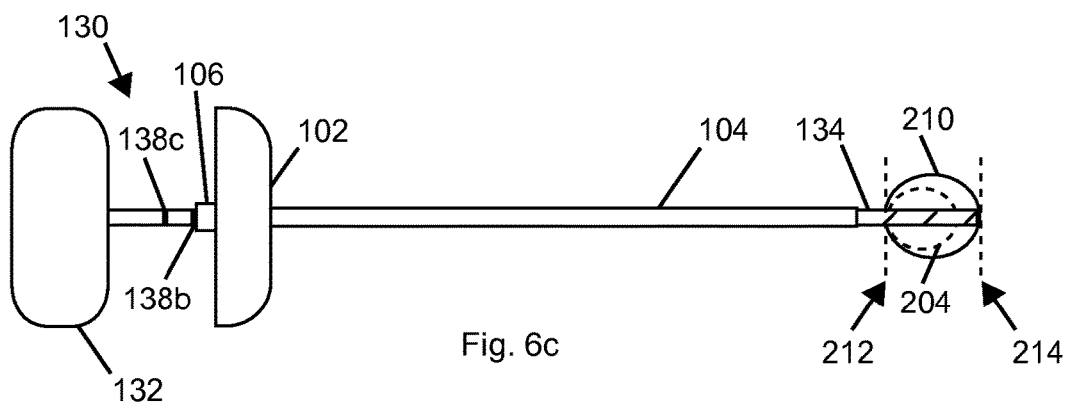
Figure 6D:
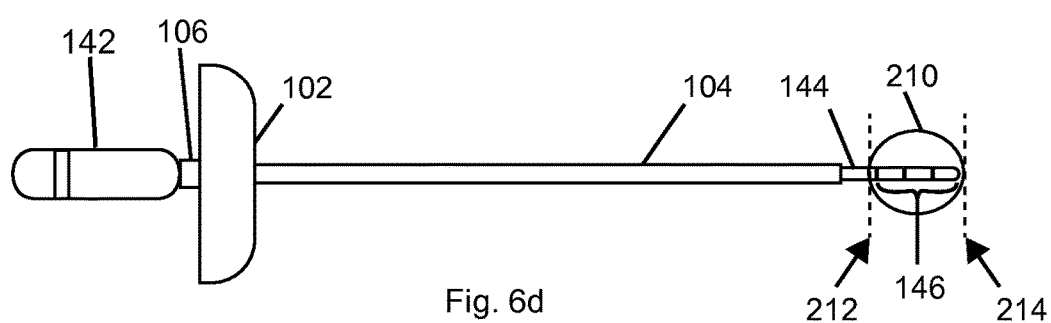

The bone drill 130 of FIG. 6b also includes three indicia, probe selection markings 138a, 138b, and 138c, longitudinally spaced along bone drill shaft 134. In the example of FIG. 6, the user advances bone drill 130 from the position of FIG. 6b to the position of FIG. 6c such that probe selection marking 138b cooperates with (i.e. lines up with) a feature of cannula 100, in this case, the proximal end of cannula 100. In FIG. 6c, the distal tip of bone drill 130 defines distal margin 214 of probe ablation zone 210. The user visualizes distal tip under imaging to map distal margin 214.

In the illustrated embodiment, a probe operable to produce ablation zone 210 corresponds with probe selection marking 138b. Alternatively, a physician could advance bone drill 130 from the position of FIG. 6b such that probe selection marking 138a lines up with the proximal end of cannula 100. Such a configuration would result in an alternate location of distal margin 214 of probe ablation zone, corresponding to the probe indicated by probe selection marking 138a. In another alternative, a physician could advance bone drill 130 from the position of FIG. 6b such that probe selection marking 138c lines up with the proximal end of cannula 100. This configuration would result in another alternate location of distal margin 214 of probe ablation zone, corresponding to the probe indicated by probe selection marking 138c. The length of a probe ablation zone mapped using probe selection marking 138a would be the shortest of the three possibly selected probes, and the length of a probe ablation zone mapped using probe selection marking 138c would be the longest of the three possibly selected probes. In the example of FIG. 6c, the probe ablation zone 210 includes material distal of desired ablation volume 204, and the physician would ensure that such material is acceptable for ablation before delivering energy.

In summary, the method includes advancing a medical instrument such as a bone drill 130 through the lumen defined by a positioned cannula 100 such that one of the indicia (probe selection marking 138) on the medical instrument indicates that a distal end of the medical instrument is positioned to define the distal margin of a probe ablation zone that may be produced by a probe corresponding with the indicia. Imaging of the positioned distal end of the medical instrument maps the distal margin of a probe ablation zone. In alternative embodiments, the indicia are selected from the group consisting of bumps, grooves, symbols and any feature that may cooperate with a feature of cannula 100. In alternative embodiments, the feature of cannula 100 is selected from the group consisting of windows, slots, detents and any feature that may cooperate with the indicia. In some embodiments, bone drill 130 has one indicium and is used with one probe. The above described method of mapping may also be used with such an embodiment.

In the embodiment of FIG. 6c, a physician maps the distal margin 214 of ablation zone 210 of the selected probe by visualizing the distal tip of the medical instrument (bone drill 130), which is positioned at distal margin 214.

Furthermore, the location of proximal margin 212 of probe ablation zone 210 is defined using the distal tip of an introducer assembly 120 (typically trocar tip 116), and the physician maps the location of proximal margin 212 by visualizing the positioned tip of introducer assembly 120. The length of the probe ablation zone is substantially equal to the distance bone drill 130 extends beyond the proximal edge 206 of desired ablation volume 204. In general, a probe ablation zone is considered to be mapped when the corresponding proximal margin 212 and distal margin 214 are mapped.

The mapped probe ablation zone provides a representation of where a corresponding probe (the probe indicated by the indicia) will ablate tissue when it delivers energy. Also, a desired ablation volume 204 is typically defined by a physician visualizing the relevant target tissue 203 using the imaging system to estimate the location of proximal edge 206 and distal edge 208 of desired ablation volume 204. Proximal edge 206 and distal edge 208 of the desired ablation volume may also be mapped using an introducer and bone drill, respectively, in the same manner as are proximal margin 212 and distal margin 214 of the probe ablation zone.

In the method of FIG. 6, the physician observes the indicium (probe selection marking 138*b*) of bone drill 130 that is aligned with a cooperating feature of the cannula (the proximal end of cannula 100) to identify the corresponding probe 140 operable to produce the mapped probe ablation zone 210. After identifying the appropriate probe, the physician then withdraws bone drill 130 from the cannula, and inserts and positions probe 140 such that the probe shaft 144 extends distal of cannula shaft 104, as shown in FIG. 6*d*. FIG. 6*d* shows probe handle 142, probe shaft 144, and active tip 146 of probe 140. The physician has advanced probe handle 142 to a stopped position, and active tip 146 is centered within probe ablation zone 210 equidistant from proximal margin 212 and distal margin 214. Energy delivered from active tip 146 typically ablates material proximal and distal of active tip 146.

The feature on cannula 100 cooperates with indicia (probe selection markings 138) of bone drill 130 to indicate which probe the physician should select to create a desired ablation result, thereby providing intra-operative probe selection for ablation. In some embodiments, probe selection markings 138*a*, 138*b* and 138*c* are color coded such that each probe selection marking corresponds with a color coding associated with each probe (e.g. probe identifier 143 of FIG. 4), thereby further aiding a physician in probe selection.

In some embodiments, a probe temperature during ablation ranges from about 40° C. to about 100° C. In other embodiments, a probe temperature during ablation ranges from about 65° C. to about 70° C. In a specific embodiment, the probe temperature during ablation is about 70° C.

In some embodiments in which the temperature of the probe during ablation is about 70° C., the probe delivers energy for a period of time ranging from about 6.5 minutes to about 15 minutes. The method may include the probe delivering energy for a period of time of about 6.5 minutes, a period of time of about 7.5 minutes, or a period of time of about 15 minutes.

One embodiment comprises a set of three color coded probes. The first probe has an active tip 7 mm long and is typically operated at a temperature of 70° C. for a period of 6.5 minutes and may produce a lesion that has a length of about 10 mm and a diameter of about 10 mm. The second probe has an active tip 10 mm long and is typically operated at a temperature of 70° C. for a period of 7.5 minutes and may produce a substantially prolate spheroid shaped lesion that has a length of about 17 mm and a diameter of about 13 mm. The third probe has an active tip 20 mm long and is typically operated at a temperature of 70° C. for a period of 15 minutes and may produce a substantially prolate spheroid shaped lesion that has a length of about 29 mm and a diameter of about 21 mm.

The method of FIG. 6 includes imaging to visualize structures of concern that a physician may wish to avoid ablating. This imaging may involve the physician mentally retaining the position of a tool after it has been moved, for example, remembering the location of the distal tip of stylet 110 after the stylet is removed. In some embodiments, the method further comprises saving a screen image as a stored image so that the stored image may be viewed at a later time. In some embodiments, the imaging system includes at least two viewing screens, and the method further includes viewing a screen image using at least two viewing screens. For example, the method may include viewing an image using different screens at different times, or transferring a screen image from one viewing screen to another.

Figure 7A:
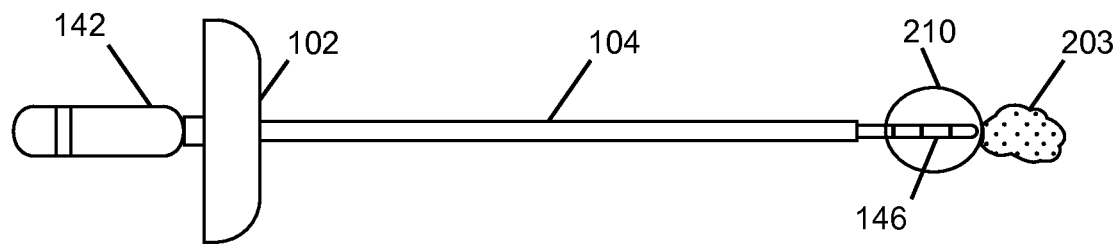
FIGS. 7a to 7d illustrate an alternative embodiment of a method of treating tissue, including the ablation of a target tissue for a situation in which the target tissue can be ablated with a second energy delivery.
Figure 7B:
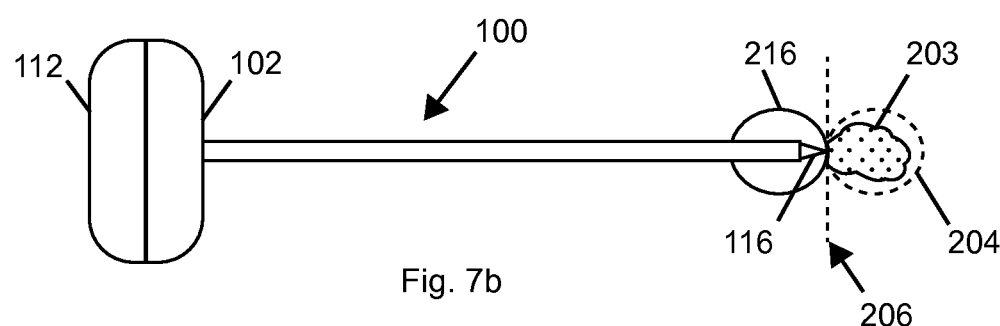
Figure 7C:
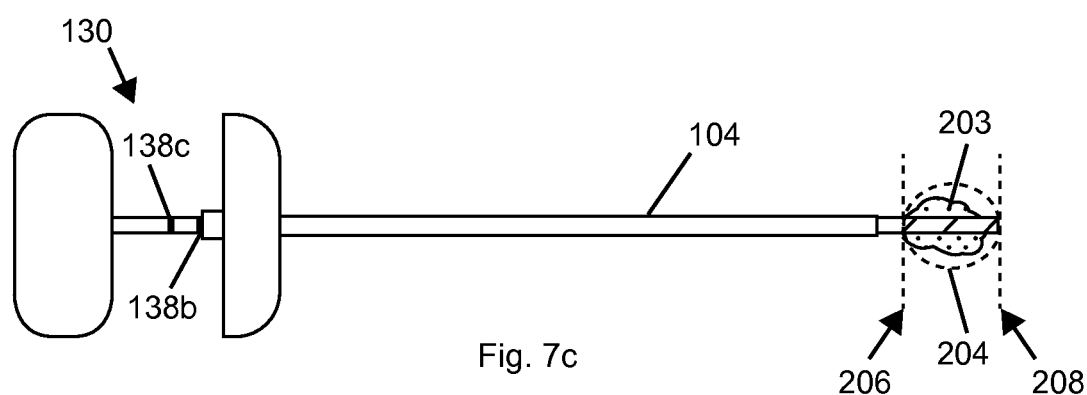

FIGS. 7*a* to 7*d* illustrate a method of ablating a target tissue for a case in which the target tissue requires a second energy delivery. FIG. 7*a* shows active tip 146 at a first location surrounded by probe ablation zone 210. The portion of target tissue inside of probe ablation zone 210 has been ablated (and consequently is not shown in FIG. 7) and the portion of the target tissue 203 outside of probe ablation zone 210 still remains. After the physician has delivered energy at the first location, the method further comprises the physician withdrawing probe 140 from cannula 100, inserting stylet 110, and advancing introducer assembly 120 to the distal margin of the probe ablation zone 210 of the first energy delivery location (FIG. 7*b*) to thereby define and, under imaging, visualize the distal tip of introducer assembly 120 to map a proximal edge 206 of desired ablation volume 204 (FIG. 7*b*) and probe ablation zone proximal margin 212 (FIG. 7*d*) of a second location. The method further comprises replacing stylet 110 with bone drill 130 (a medical instrument), advancing bone drill 130 until an indicium (probe selection marking 138) lines up with a corresponding feature of the cannula to position the distal tip of the bone drill 130 at the distal edge 208 of desired ablation volume 204, and visualizing the positioned tip to map the distal edge 208 (FIG. 7*c*) and a probe ablation zone distal margin 214 (FIG. 7*d*) of the second location.

Figure 7D:
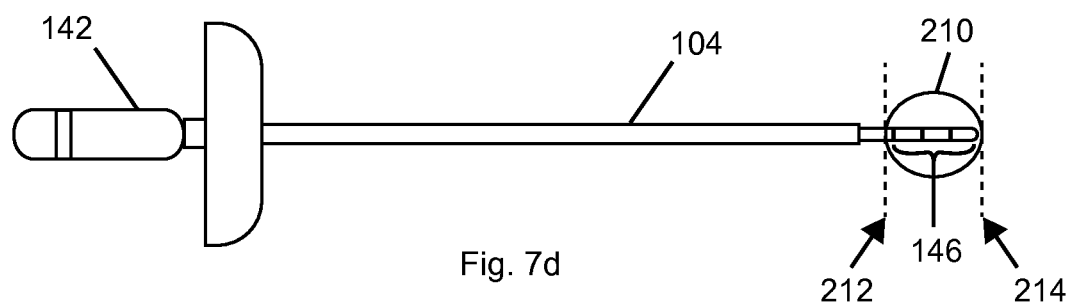

In other words, the physician determines that bone drill 130 is positioned for mapping by one of the indicia (probe selection marking 138*b*) lining up with the cooperating feature of the cannula (the cannula proximal end). Probe selection marking 138*b* also indicates the corresponding probe operable to produce the mapped ablation zone of FIG. 7*d*. The physician selects the corresponding probe and replaces bone drill 130 with the probe. The length of the probe ablation zone 210 of FIG. 7*d* is substantially equal to a distance the bone drill 130 extends beyond the proximal edge 206 of desired ablation volume 204 of FIG. 7*c*. In the example of FIG. 7, desired ablation volume 204 and probe ablation zone 210 have substantially the same mapping (i.e. proximal edge 206 of desired ablation volume 204 is the same as probe ablation zone proximal margin 212 and distal edge 208 of desired ablation volume 204 is the same as probe ablation zone distal margin 214).

Figure 8A:
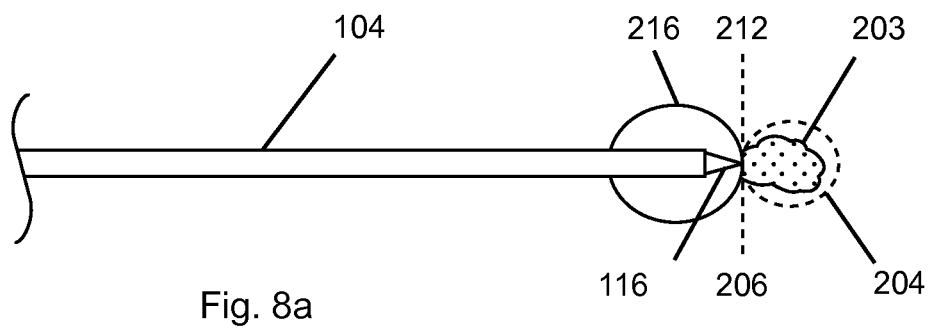
FIG. 8a illustrates an introducer assembly positioned after a first ablation of target tissue requiring a second ablation.

FIG. 8*a* illustrates a case of a target tissue that requires a second delivery of energy for ablation. FIG. 8*a* includes previous ablation 216 created by the first delivery of energy; a trocar tip 116 of an introducer assembly that, after the first delivery of energy, was positioned against the distal margin of previous ablation 216; the remaining portion of target tissue 203; and a desired ablation volume 204 for a second delivery of energy. Desired ablation volume 204 has a proximal edge 206 equivalent to (i.e. at the same location as) proximal margin 212 of probe ablation zone 210 (FIG. 8*b*) for a second delivery of energy.

Figure 8B:
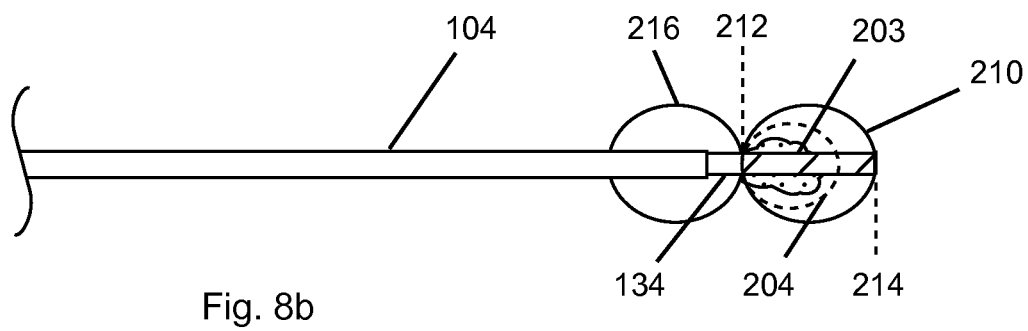
Figure 8C:
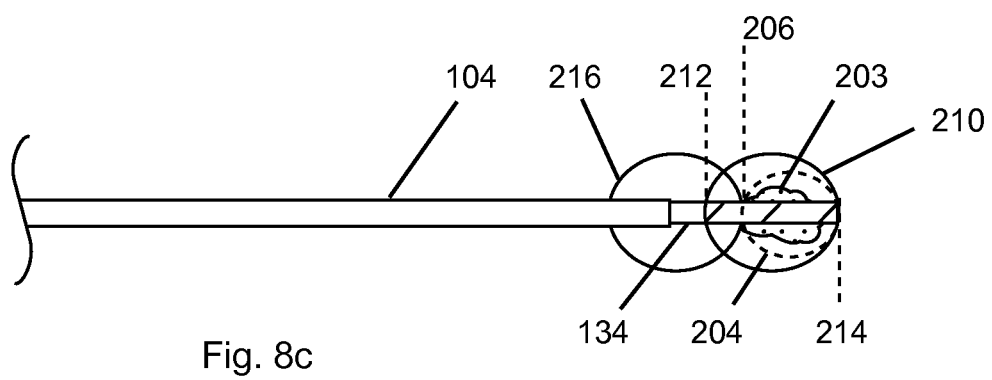
Figure 8D:
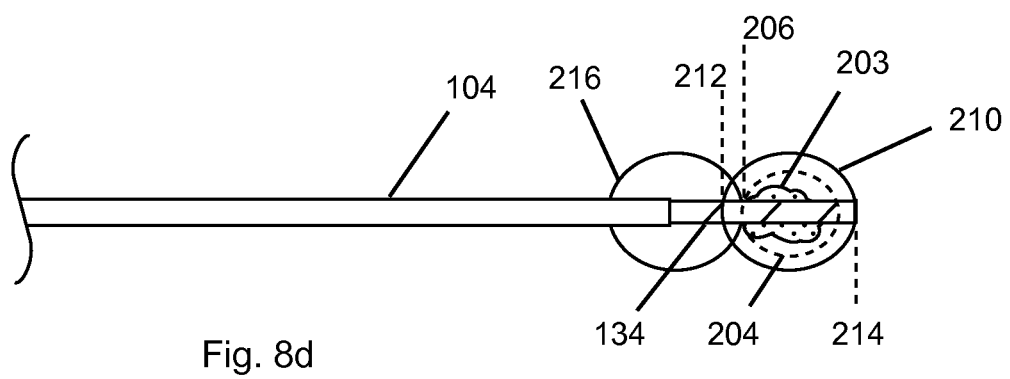

FIGS. 8b to 8d illustrate alternative methods of treating the remaining portion of the target tissue of FIG. 8a.

FIG. 8b illustrates a bone drill that a physician has advanced such that an indicium is lined up with a corresponding feature on a cannula whereby the distal tip of a bone drill shaft 134 (the medical instrument) defines distal margin 214 of probe ablation zone 210. The distal tip of bone drill shaft 134 is positioned distal of (i.e. beyond) the distal edge of the desired ablation volume 204 of the second energy delivery location. A method of ablating the remaining portion of target tissue 203 of FIG. 8b comprises confirming that the tissue within of the probe ablation zone 210 and outside of the desired ablation volume 204 is acceptable for ablation, selecting the corresponding probe indicated by the probe selection marking used to position the bone drill, withdrawing the medical instrument from the cannula and inserting the selected probe, and delivering energy to ablate the tissue in probe ablation zone 210. The step of confirming that tissue within the probe ablation zone is acceptable for ablation includes the physician checking for any anatomical features within the probe ablation zone that should not be subjected to energy delivery.

FIG. 8c shows the distal end of bone drill shaft 134 positioned at the distal edge of desired ablation volume 204. A method associated with FIG. 8c comprises the following steps: positioning an introducer assembly with a trocar tip 116 as described above for FIG. 8a; positioning a bone drill with a bone drill shaft 134 as described above for FIG. 8b; withdrawing both of the cannula and the bone drill until the distal tip of the bone drill is positioned at the distal edge of the desired ablation volume 204 (as shown in FIG. 8c) and the cannula is positioned proximal of the remaining portion of target tissue 203 while the indicium of the bone drill used to define distal margin 214 of probe ablation zone 210 remains lined up with a corresponding feature of the cannula (distal margin 214 is still defined); visualizing the distal tip of the positioned bone drill 130 to define distal margin 214 of probe ablation zone 210 and estimating the proximal margin 212 of the probe ablation zone based on the visualized position of the distal tip of cannula 100 to thereby map probe ablation zone 210; selecting the corresponding probe as indicated by the indiciuma used to define distal margin 214; withdrawing the bone drill from the cannula and inserting the probe; and delivering energy to ablate tissue within the probe ablation zone 210.

FIG. 8d shows the distal end of bone drill shaft 134 positioned distal of desired ablation volume 204 and the tip of cannula shaft proximal of desired ablation volume 204 such that desired ablation volume 204 is inside probe ablation zone 210. A method associated with FIG. 8d comprises the following steps: positioning an introducer assembly with a trocar tip 116 as described above for FIG. 8a; positioning a bone drill with a bone drill shaft 134 as described above for FIG. 8b; withdrawing both of the cannula and medical instrument (the bone drill) while maintaining the position of the distal tip of the bone drill distal of the distal edge of the desired ablation volume 204 and positioning the cannula such that it is proximal of the target tissue 203 while the indicium of the bone drill used to define distal margin 214 of probe ablation zone 210 remains lined up with a corresponding feature of the cannula (whereby distal margin 214 is still defined); mapping probe ablation zone 210 by visualizing the distal tip of the positioned bone drill 130 to map distal margin 214 of probe ablation zone 210 and visualizing the distal tip of cannula 100 to thereby estimate the position of the proximal margin 212 of the probe ablation zone; selecting the corresponding probe as indicated by the indiciuma used to define distal margin 214; withdrawing the bone drill from the cannula and inserting the probe; and delivering energy to ablate tissue within probe ablation zone 210.

The step of withdrawing and positioning the cannula and the bone drill is done such that the defined probe ablation zone 210 includes the desired ablation volume 204. It is optional for the physician to attempt to position the bone drill 130 and cannula such that the desired ablation volume is centered within the defined probe ablation zone 210 as illustrated in the example of FIG. 8d. In one embodiment of the method, centering the desired ablation volume 204 within the probe ablation zone 210 includes positioning the tip of the bone drill a distance distal of the distal edge of the desired ablation volume that is substantially equal to the distance the tip of the cannula is positioned proximal of the proximal edge of the desired ablation volume. In other words, the position of the distal tip of the bone drill, and the position of the tip of the trocar tip 116 are equidistant from the remaining portion of the target tissue.

Figure 9A:
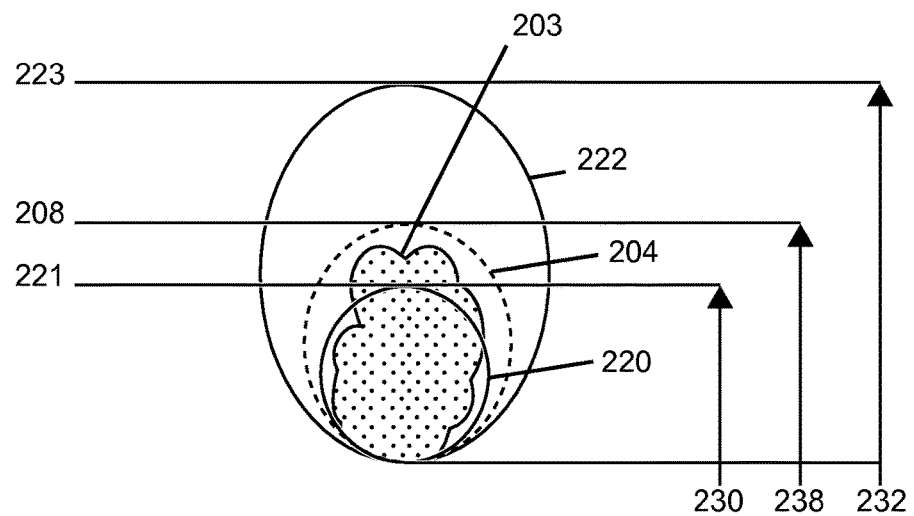
FIG. 9a illustrates the probe ablation zones of first and second probes relative to a target tissue and an associated desired ablation volume.
Figure 9B:
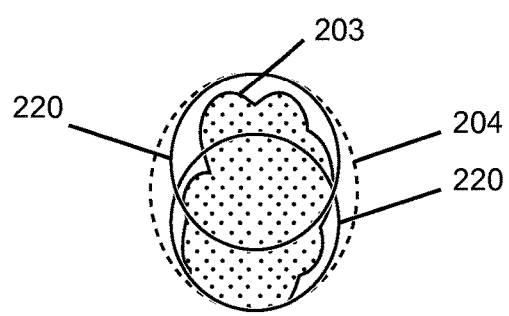
Figure 9C:
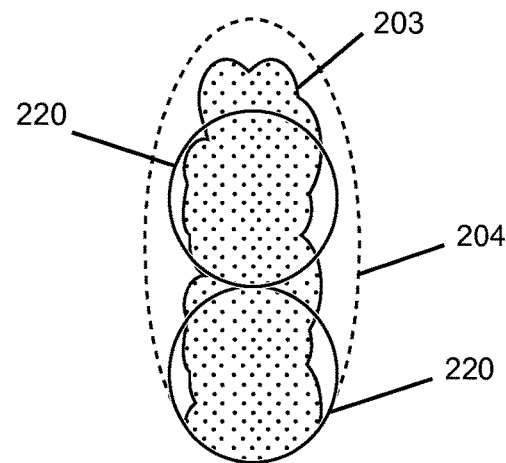
FIG. 9c illustrates a method of treating an alternative shaped target tissue.

FIGS. 9a to 9c also relate to cases that require more than a single energy delivery to ablate a target tissue 203. FIGS. 9a to 9c illustrate the strategy of mapping the probe ablation zones of two probes before ablating tissue, wherein one probe has a longer ablation zone length 232 greater than the target tissue longitudinal length, and one probe has a shorter ablation zone length 230. FIG. 9a is a diagram illustrating the probe ablation zones 220 and 222 of first and second probes, relative to a target tissue 203 and associated desired ablation volume 204. FIG. 9b illustrates a strategy for using the first probe to treat the target tissue of FIG. 9a. FIG. 9c illustrates a strategy for using the first probe to treat an elongated target tissue.

Starting from the situation of FIG. 7a, which shows a treatment tissue that has been partially ablated using a probe having a probe ablation zone 210, and arriving at situation shown in FIG. 9a, the steps of a method are as follows: withdrawing probe 140 (FIG. 7a) and inserting stylet 110; advancing introducer assembly 120 to the distal margin of probe ablation zone 210 of the first location (as shown in FIG. 8a) to define a probe ablation zone proximal margin of a second location, then visualizing the positioned distal tip of introducer assembly 120 to map a probe ablation zone proximal margin of the second location (FIG. 9a); imaging target tissue 203 (FIG. 9a); replacing the stylet with a bone drill and advancing the bone drill until an indicium lines up with the corresponding feature of the cannula and the distal tip is at or beyond the distal edge of the desired ablation volume 204, where it defines the probe ablation zone distal margin 221 of the first probe; visualizing a positioned distal tip of a bone drill to map probe ablation zone distal margin 221 of the first probe, which is proximal of distal edge 208 of a desired ablation volume 204; advancing the bone drill until another indicium lines up with the corresponding feature of the cannula, at which time the positioned tip of the bone drill defines probe ablation zone distal margin 223 of the second probe; visualizing a positioned distal tip of a bone drill to map probe ablation zone distal margin 223 of the second probe, which is distal of distal edge 208 of a desired ablation volume 204; and using the imaging system to compare the probe ablation zones of the first and second probes to the desired ablation volume (i.e. comparing probe ablation zone distal margin 221 of the first probe and probe ablation zone distal margin 223 of the second probe to distal edge 208 of the desired ablation volume).

The method of FIG. 9 includes selecting and positioning a probe for ablating at the second location such that subsequent lesions would result in an overall effective or efficient ablation procedure, based on the comparisons of the probe ablation zones and the desired ablation volume. In some alternative embodiments, target tissue 203 may not be imaged using intraoperative CT. Instead, the location of target tissue may be known by reference to other anatomical landmarks, or through prior knowledge from a different imaging modality that is not available during ablation (such as magnetic resonance imaging).

In the example of FIG. 9b, the probe ablation zone length of the first probe is greater than 50% of a length of the desired ablation volume. In this example, the method further comprises planning to position the first probe at two positions for two deliveries of energy whereby it is possible to produce overlapping probe ablation zones that will ablate the desired ablation volume. In the example of FIG. 9b, the probe ablation zone 220 at the bottom of the figure overlaps with the probe ablation zone 220 at the top of the figure, and the top probe ablation zone has a distal margin located substantially at or beyond the distal edge of the desired ablation volume. In the example of FIG. 9b, the same probe is used for both deliveries of energy, but in alternative embodiments, two probes could be used to produce different sized probe ablation zones.

In the embodiment of FIG. 9c, target tissue 203 is elongated relative to the target tissue of FIGS. 9a and 9b, but the steps up to and including comparing the probe ablation zones and desired ablation volume are the same. In FIG. 9c the ablation zone length of the first probe at the second location (ablation zone 220 at the bottom in FIG. 9c) is less than 50% of a length of the desired ablation volume. The probe ablation zone length of the first probe at the second location and another probe ablation zone length (ablation zone 220 at the top in FIG. 9c) add up to less than a length 238 of the desired ablation volume. The method of this embodiment further comprises planning to position the probe at two positions such that delivering energy at the two positions will produce probe ablation zones that are end-to-end, as shown in the example of FIG. 9c. As with FIG. 9b, the probe used at the two positions is the same probe, but in alternative embodiments, different probes could be used to produce different sized probe ablation zones. The method of FIG. 9c would require another ablation at another position to completely ablate target tissue 203.

In alternative embodiments of the method, after comparing the probe ablation zones and desired ablation volume of FIG. 9a, the physician could use the second probe for ablation (i.e. the probe operable to produce probe ablation zone 222 shown in FIG. 9a). Probe ablation zone 222 has a distal margin 223. In this embodiment, the method further includes confirming that the probe ablation zone of the second probe outside of the desired ablation volume is acceptable, selecting the second probe, and supplying energy to the probe for ablating tissue. As previously described, the step of confirming that tissue within probe ablation zone 222 is acceptable for ablation includes the physician checking for any anatomical features that should not be subjected to energy delivery.

With appropriate modifications, the above methods of comparing probe ablation zones and the desired ablation volume to plan for probe positioning as described for FIG. 9 can also be applied in the first ablation of target tissue, as would be understood by one of skill in the art.

The above described methods of positioning a probe for a second ablation of target tissue as described with respect to FIG. 8 can also be used in the first ablation of target tissue, as will now be described making reference to FIG. 10.

Figure 10A:
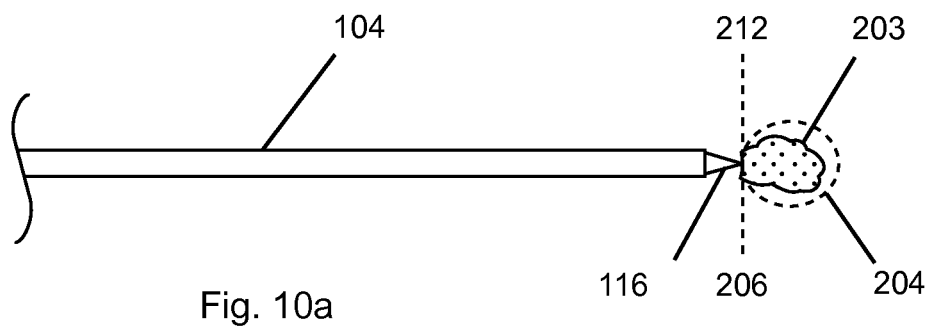
FIG. 10a illustrates an introducer assembly positioned before a first ablation of target tissue.

FIG. 10a illustrates the case of a target tissue that requires only one delivery of energy for ablation, but the probe ablation zone is longer than the length 238 of the desired ablation volume. FIG. 10a includes target tissue 203; a trocar tip 116 of an introducer assembly positioned against target tissue 203; and a desired ablation volume 204. Desired ablation volume 204 has a proximal edge 206 equivalent to (i.e. at the same location as) proximal margin 212 of probe ablation zone 210, as shown in FIG. 10b.

Figure 10B:
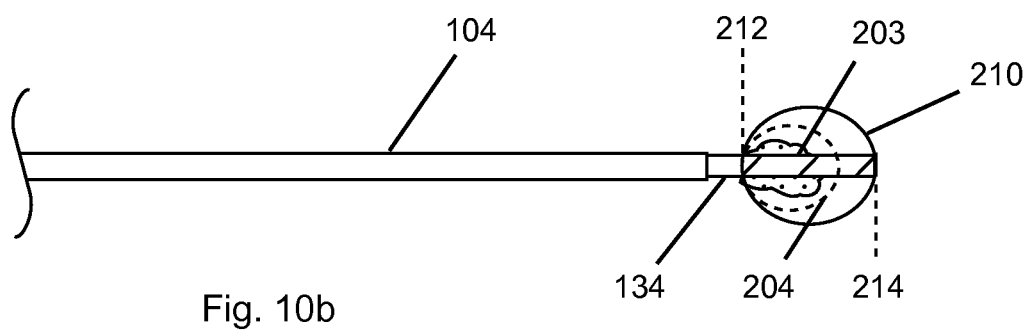
Figure 10C:
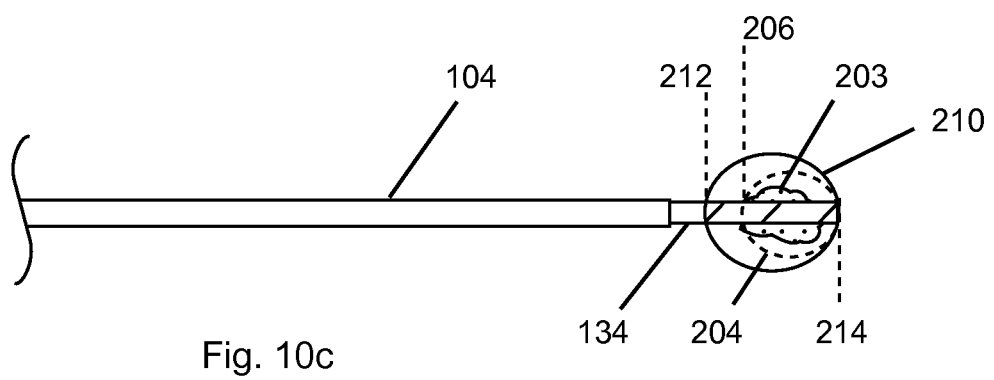
Figure 10D:
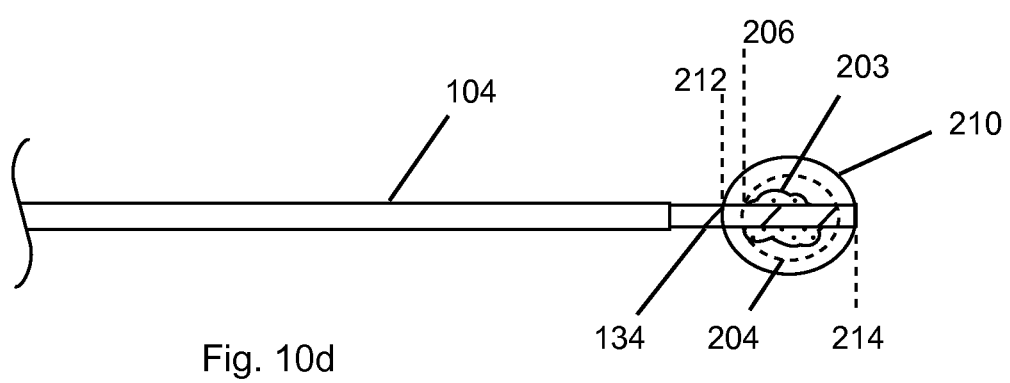

FIGS. 10b to 10d illustrate alternative methods of treating the target tissue of FIG. 10a.

FIG. 10b illustrates a bone drill that a physician has advanced to line up an indicium with a corresponding feature on a cannula such that the distal tip of a bone drill shaft 134 (the medical instrument) defines distal margin 214 of probe ablation zone 210. The distal tip of bone drill shaft 134 is positioned distal of (i.e. beyond) the distal edge of the desired ablation volume 204. A method of ablating the target tissue 203 of FIG. 10b comprises the following steps: confirming that the tissue within the probe ablation zone 210 and outside of the desired ablation volume 204 is acceptable for ablation; selecting the corresponding probe indicated by the probe selection marking used to position the bone drill; withdrawing the bone drill from the cannula and inserting the selected probe; and delivering energy to ablate the tissue in probe ablation zone 210. The step of confirming that tissue within the probe ablation zone is acceptable for ablation includes the physician checking for any anatomical features that should not be submitted to energy delivery.

FIG. 10c shows the distal end of bone drill shaft 134 positioned at the distal edge of desired ablation volume 204. A method associated with FIG. 10c comprises the following steps: positioning an introducer assembly with a trocar tip 116 as described above for FIG. 10a; positioning a bone drill with a bone drill shaft 134 as described above for FIG. 10b; withdrawing both of the cannula and the bone drill until the distal tip of the bone drill is positioned at the distal edge of the desired ablation volume 204 (as shown in FIG. 10c) and the cannula is positioned proximal of the remaining portion of target tissue 203 while the indicium of the bone drill used to define distal margin 214 of probe ablation zone 210 remains lined up with a corresponding feature of the cannula (distal margin 214 is still defined); visualizing the distal tip of the positioned bone drill 130 to define distal margin 214 of probe ablation zone 210 and estimating the proximal margin 212 of the probe ablation zone based on the visualized position of the distal tip of cannula 100 to map probe ablation zone 210; selecting the corresponding probe as indicated by the indicium used to define distal margin 214; withdrawing the bone drill from the cannula and inserting the probe; and delivering energy to ablate tissue within the probe ablation zone 210.

FIG. 10d shows the distal end of bone drill shaft 134 positioned distal of desired ablation volume 204, and the tip of cannula shaft proximal of desired ablation volume 204 such that desired ablation volume 204 is inside probe ablation zone 210. A method associated with FIG. 10d comprises the following steps: positioning an introducer assembly with a trocar tip 116 as described above for FIG. 10a; positioning a bone drill with a bone drill shaft 134 as described above for FIG. 10b; withdrawing both of the cannula and medical instrument (the bone drill) while maintaining the position of the distal tip of the bone drill distal of the distal edge of the desired ablation volume 204 and positioning the cannula proximal of the target tissue 203 while the indicium of the bone drill used to define distal margin 214 of probe ablation zone 210 remains lined up with a corresponding feature of the cannula (whereby distal margin 214 is still defined); mapping probe ablation zone 210 by visualizing the distal tip of the positioned bone drill 130 to map distal margin 214 of probe ablation zone 210 and visualizing the distal tip of cannula 100 to estimate the position of the proximal margin 212 of the probe ablation zone; selecting the corresponding probe as indicated by the indicium used to define distal margin 214; withdrawing the bone drill from the cannula and inserting the probe; and delivering energy to ablate tissue within probe ablation zone 210.

The step of withdrawing and positioning the cannula and the bone drill is done such that the defined probe ablation zone 210 includes the desired ablation volume 204. It is optional for the physician to attempt to position the bone drill 130 and cannula such that the desired ablation volume 204 is centered within the defined probe ablation zone 210, as illustrated in the example of FIG. 10d.

FIG. 11 illustrates an embodiment of a method of ablating a target tissue that requires more than one ablation. In this embodiment, the furthermost or most distal ablation is performed first. FIG. 11a shows an introducer assembly 120 positioned inside of a target tissue (not shown in FIG. 11). The parts of introducer assembly 120 shown in FIG. 11 include trocar tip 116 (of stylet 110), and cannula shaft 104 of cannula 100. The method includes removing stylet 110, inserting bone drill 130 (indicated by bone drill shaft 134 in FIG. 11b) and advancing bone drill 130 (the medical instrument) until the distal tip of the bone drill is at the distal edge 208 of the desired ablation volume (shown in FIG. 11b), at which time the distal tip of bone drill 130 will define a distal edge 208 of desired ablation volume 204 and a distal margin 214 of probe ablation zone 210. The method further includes withdrawing cannula 100 a distance d1, shown by arrow d1 of FIG. 11c, until one of the indicia (e.g. probe selection markings 138) lines up with the corresponding feature of cannula 100, while the bone drill is held in position such that the distal tip of bone drill 130 still defines distal margin 214 of probe ablation zone 210 (FIG. 11c). The method includes visualizing the distal tip of bone drill 130 (before or after positioning cannula in accordance with FIGS. 11b and 11c) to map distal margin 214 of probe ablation zone 210, removing bone drill 130 from the cannula, and inserting a probe 140 (indicated by probe shaft 144 in FIG. 11d). The user then advances probe 140 until it is at the ablation position of the selected probe. Energy is delivered from active tip 146 of probe 140 and forms a lesion corresponding to probe ablation zone 210 of FIGS. 11d and 11e. In the embodiment of FIG. 11d, a gap remains between the ablation zone 210 and the tip of cannula 100.

Following the delivery of energy, probe 140 is withdrawn and bone drill 130 re-inserted into cannula 100. It is not necessary to re-install the stylet as is done when advancing an introducer assembly after an ablation. Bone drill 130 is advanced until it protrudes from the distal end of cannula 100 a distance about equal to the distance which stylet 110 protrudes from cannula 100 when the stylet is fully inserted (which is about the same as the distance of the above mentioned gap of FIG. 11d). In this configuration, the tip of bone drill 130 should be at the distal margin of the probe ablation zone 210 of FIG. 11e. In this position, the bone drill 130 defines a distal edge 208 of the next desired ablation volume and a distal margin 214 of the next probe ablation zone 210. Subsequent to bone drill 130 being positioned as shown in FIG. 11e, cannula 100 is withdrawn a distance d2, shown by arrow d2 of FIG. 11f, until one of the indicia lines up with the corresponding feature, at which time the distal tip of bone drill 130 still defines a distal edge 208 of the next desired ablation volume 204.

Figure 11A:
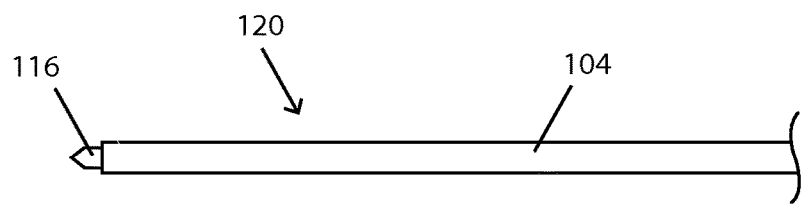
FIGS. 11a to 11g illustrate an embodiment of a method of positioning an apparatus for treating tissue.
Figure 11B:
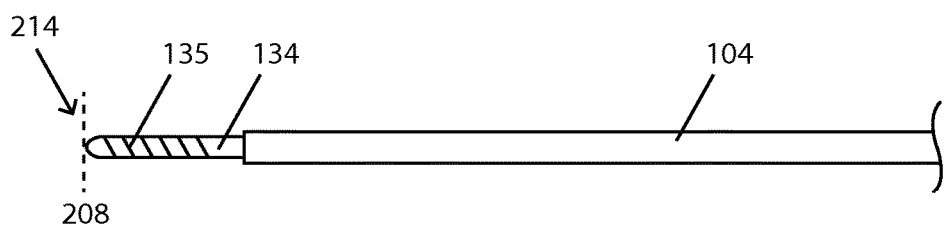
Figure 11C:
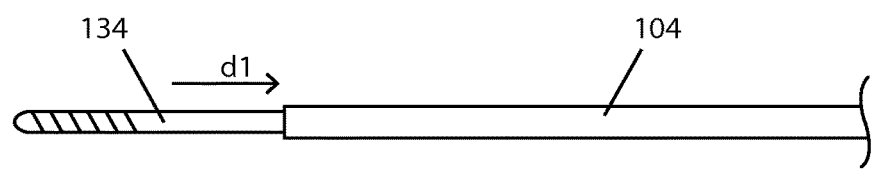
Figure 11D:
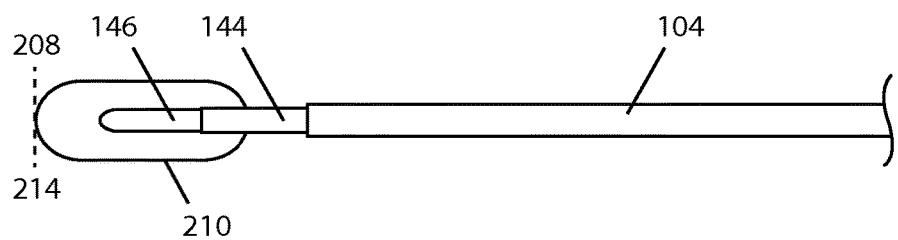
Figure 11E:
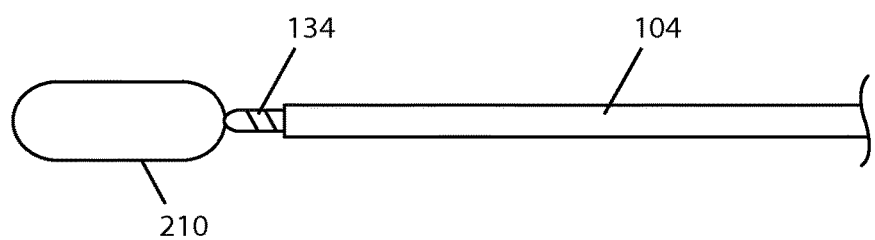
Figure 11F:
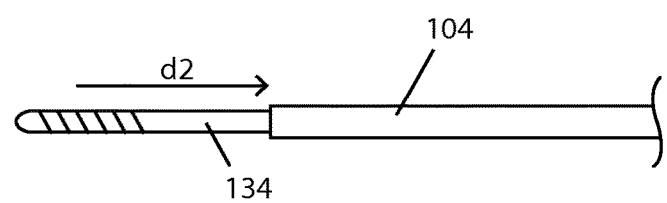
Figure 11G:
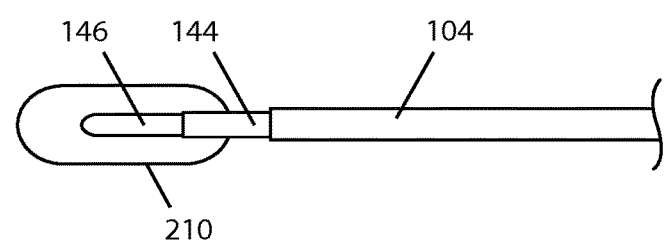

At the physician's discretion, he/she may withdraw the cannula a distance to line up a different indicium than used for the FIG. 11c positioning, and map a different probe ablation zone than that of FIG. 11d, and correspondingly, select a different probe for ablation. The steps after defining distal edge 208 of the next desired ablation volume 204 are the same as described above to arrive at the situation of FIG. 11g. FIG. 11g shows a probe with active tip 146 and a corresponding probe ablation zone 210 that is substantially the same in size as the probe ablation zone of FIG. 11d. The method may include additional ablations, if needed.

FIGS. 12a to 12c illustrate an embodiment related to imaging for marking the side or radial boundaries of a probe. The apparatus shown in FIG. 12 includes a bone drill including a bone drill shaft 134, helical flutes 135, and bone drill handle 132. Attached or mounted on drill shaft 134 is an imaging tool comprising a collar 246 (shown in FIGS. 12b and 12c) having a center hole 248 for receiving bone drill shaft 134, and a first extending member 242 and a second extending member 242, each extending out from the collar 246 so as to be extending radially from shaft 134. Alternative embodiments of the imaging tool may have only one extending member 242. Embodiments of the imaging tool comprise one or more shadow casting pieces 244. In the embodiment of FIG. 12a, each extending member has more than one shadow casting piece 244 comprised of a radiopaque material. Each shadow casting piece 244 is spaced apart from the center hole.

In use, an imaging system projects X-rays from a location in-line with the shaft 134 and proximal of the imaging tool to cast shadows visible using the imaging system and corresponding to each of the shadow casting pieces 244. The shadow casting pieces of the first extending member and the shadow casting pieces of the second extending member comprise pairs that are equidistant from the collar. The first pair of shadow casting pieces 244 cast a pair of shadows defining opposite side radial margins of a probe ablation zone of a corresponding first probe (not show in picture). Each pair of shadow casting pieces has an indicium 250 corresponding with a probe.

FIGS. 12b and 12c illustrate alternative embodiments of imaging tool 240. An imaging tool 240 includes at least one imaging tool indicium 250 for each pair of shadow casting pieces. Each imaging tool indicium 250 corresponds with a probe having side or radial margins corresponding with the shadows cast by the shadow casting pieces.

In use, X-rays projected by an imaging system will strike all the radiopaque shadow casting pieces, causing shadows to be cast for all of the pieces. For explanatory purpose, FIG. 12a illustrates this with respect to a first or innermost shadow casting piece 244. As seen in FIG. 12a, an imaging system projects X-rays that strike a first radiopaque shadow casting piece 244 (a first member visualization element). The two broken lines represent the projection lines of a pair of shadow casting pieces. The broken lines define the radial margins of a first probe. Each pair of shadow casting pieces defines the radial margins of a corresponding probe. Upon seeing the shadows cast by the apparatus, a user may select a probe corresponding to one of the pairs by referring to the imaging tool indicia 250, each of which corresponds with a specific probe.

The concepts of the above method can be applied in other types of imaging systems other than X-ray systems in which first member and second member visualization elements are used.

FIG. 12d illustrates an example of the use of the embodiment of FIGS. 12a to 12c for mapping side-by-side probe ablation zones. The method includes the following steps: (a) positioning a medical instrument with an imaging tool installed on a proximal end of the medical instrument to be in-line and proximal of a treatment site, (b) projecting X-rays from an imaging system positioned in-line and proximal of the medical instrument to cast a pair of shadows defining a probe ablation zone 210a of the probe at a first position, (c) mapping the probe ablation zone using the imaging system, (d) mapping at least one imaging system marker 258 at an edge of the probe ablation zone at the first position, (e) moving the medical instrument with the imaging tool side-ways to a second position, and (f) projecting X-rays from the imaging system positioned in-line and proximal of the medical instrument to cast a pair of shadows defining the probe ablation zone 210b of the probe at the second position.

FIG. 12d(i) illustrates an example of when the probe ablation zones of the first position 210a and the second position 210b are side-by-side and adjacent. FIG. 12d(ii) illustrates an example of when the probe ablation zones of the first position and the second position are slightly overlapping. FIG. 12d(iii) illustrates the further step of mapping at least one imaging system marker 258 at the edge of the probe ablation zone at the second position. While the embodiments of FIG. 12d show the case where the boundaries of the same probe is being imaged for the first and second position, alternative embodiments include using the method for probes with different probe ablation zones.

Figures 13A, 13B:
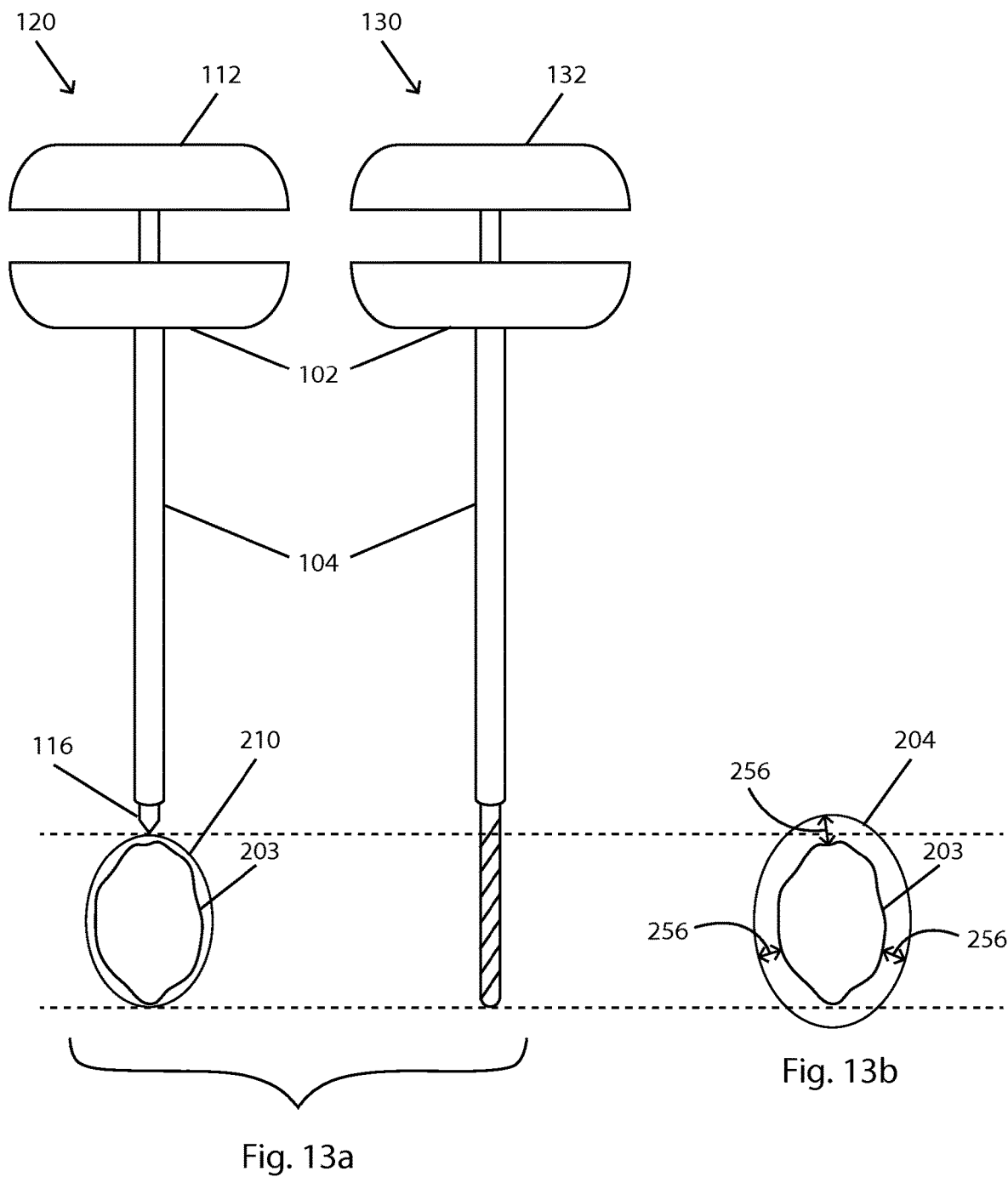
FIGS. 13a and 13b illustrate an embodiment related to an expanded margin.

FIG. 13 illustrates an embodiment of a method for providing an expanded margin to ensure that a target tissue is ablated. FIG. 13a illustrates the previously described positioning of a cannula (indicated by cannula shaft 104), a stylet (indicated by stylet handle 112), and medical instrument (indicated by bone drill handle 132) to determine a probe ablation zone 210. In this case, the probe ablation zone 210 corresponds in extent (but not exactly) with target tissue 203. Once a physician has determined that a probe ablation zone corresponds (approximately or exactly) with a target tissue, he/she may select a margin 256 around the ablation zone to provide an effective ablation of the target tissue, and selectively alter a probe variable to provide the desired ablation volume 204. In some embodiments of the method, a physician may select a probe with a larger ablation zone than that of FIG. 13a, such that the selected probe has a probe ablation zone corresponding to the desired ablation zone 204 of FIG. 13b, thereby providing the safety margin 256.

In other embodiments, a physician may select a probe with the probe ablation zone 210 of FIG. 13a under normal operating conditions, and adjust a power system connected to the probe to provide greater power, in a manner known to those skilled in the art, whereby the probe ablates tissue corresponding to the desired ablation zone 204 of FIG. 13b, thereby providing the safety margin 256.

Figure 14A:
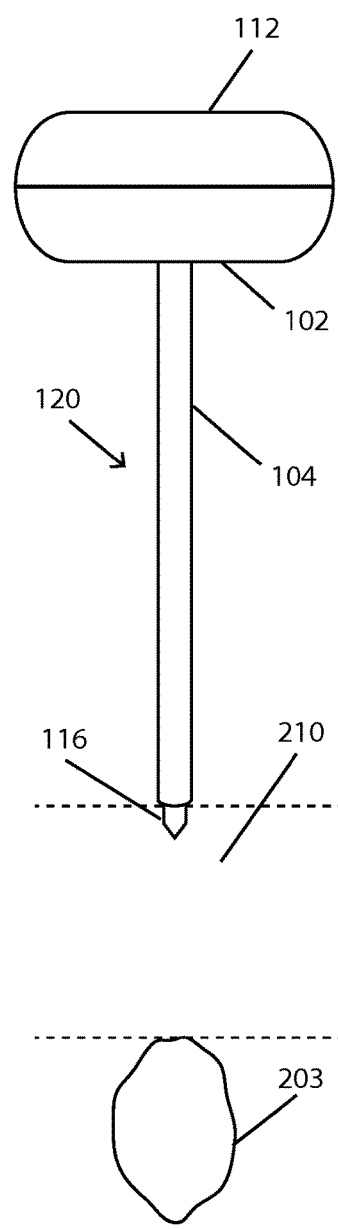
Figure 14B:
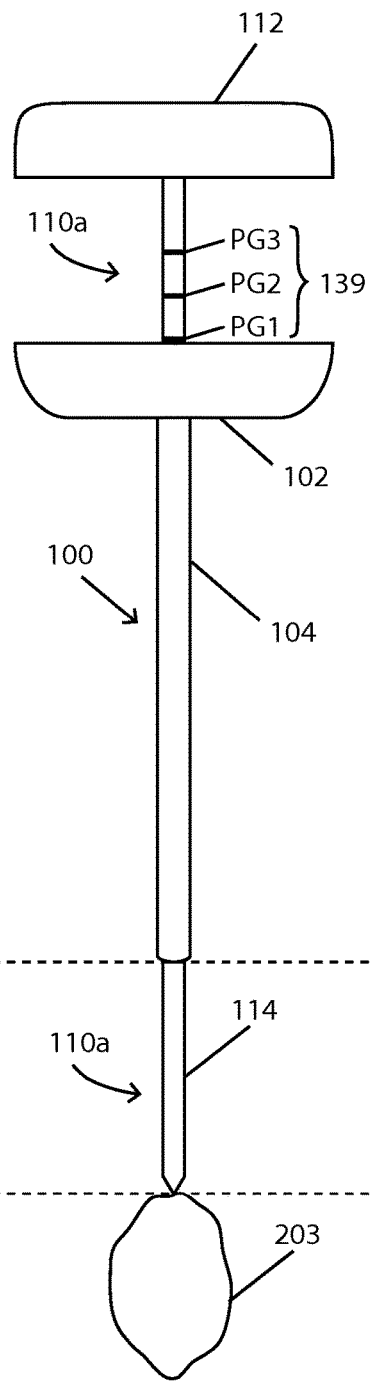

The apparatus of FIG. 14 is similar to previously described apparatus but with the stylet 110a being longer (relative to the cannula) than previously illustrated examples, and the stylet having the additional feature of probe group markings 139. In the example of FIG. 14b, PG1, PG2, and PG3 each correspond to a group of probes. Each group has an associated medical instrument.

Figure 14C:
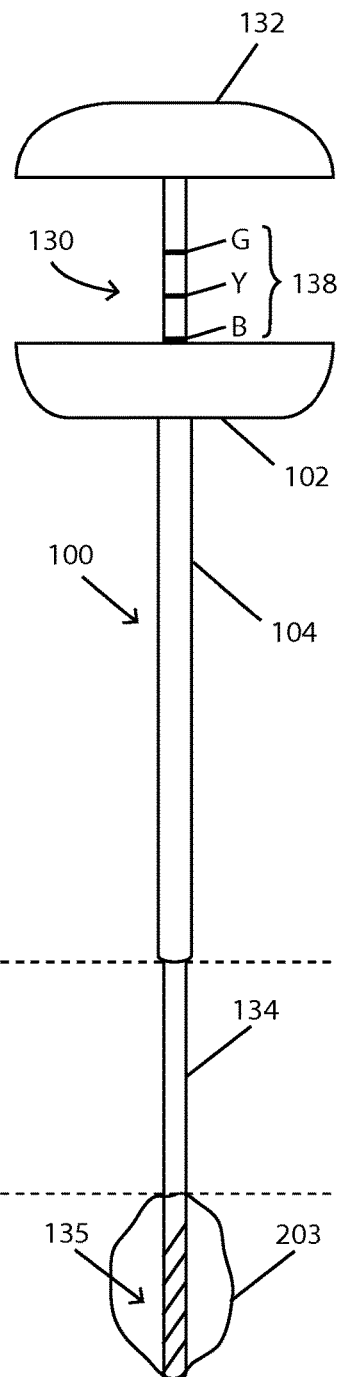

In the example of FIG. 14, the cannula cannot or should not be advanced to the edge of target tissue 203 due to a sensitive body structure. A physician advances elongated stylet 110a until its tip is at the edge of the target tissue, at which time a probe group marking 139 (PG1 in this example) aligns with a cooperating structure on the cannula 100 and thereby indicates which bone drill 130 to use for selecting a probe from within a group of probes. FIG. 14c illustrates a bone drill advanced to the far side of target tissue 203 and a probe section marking 138 (in this case marker B) aligned with the cooperating cannula feature to indicate which probe to use for ablation. In this example, the probe section markings are B, Y, and G, and correspond with color coded probes. Color coded probes facilitate selecting a probe during a medical procedure.

FIG. 14d is a table representing an example of a system having nine probes, P1 to P9. Probes P1 to P3 of row 1 are in probe group PG1, and are associated with a bone drill (coded 100). The other two rows represent different probe groups and associated bone drills. Each group of probes is color coded as B, Y, and G (blue, yellow, and green). The colors also correspond with indicia on the associated bone drill.

Figures 15A, 15B, 15C:
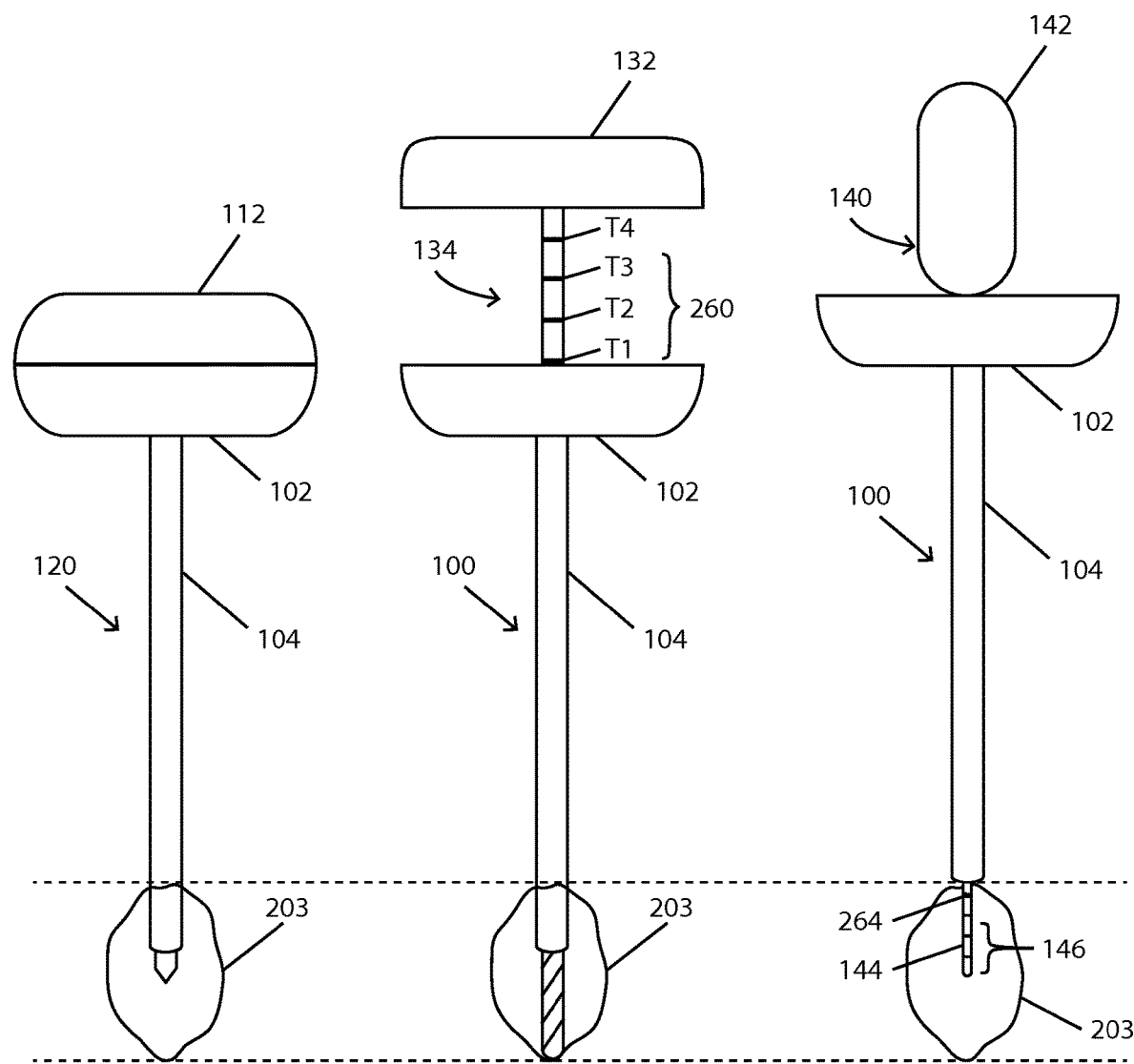
FIGS. 15a to 15c illustrate an embodiment related to probe temperature.

FIG. 15 illustrates an embodiment in which the apparatus provides a temperature setting for the probe. In this embodiment, the introducer assembly 120 is positioned with its tip in the center of target tissue 203 (not at the edge as previously described for some other embodiments). A medical instrument with temperature selection markings 260 is advanced until its tip reaches the distal side of target tissue 203. The medical instrument is advanced a greater distance for a larger target tissue. A temperature selection marking 260 indicates which temperature is used for ablation. In the example of FIG. 15b, T1 is aligned with a cooperating feature of cannula handle 102. Since the medical instrument is advanced further for larger targets, the temperature selection markings further up (in the positioning of FIG. 15) correspond with higher temperature settings. For example, T4 corresponds to a higher temperature setting than T1. If the cooperating feature is between two temperature selection markings, the procedure temperature can be interpolated from the two associated temperatures.

FIG. 15c illustrates a probe that has been positioned with its active tip 146 in the center of the target tissue 203 for ablation. The probe has a radiopaque marker 264 to aid in positioning.

Figure 16:
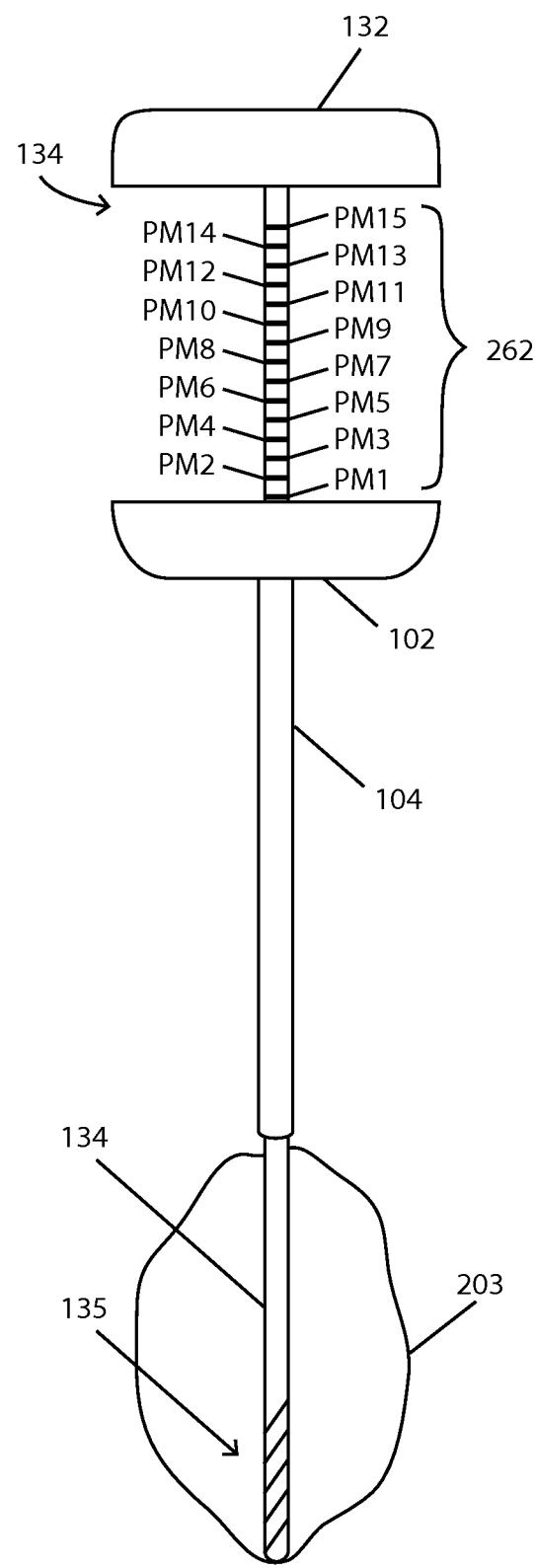
FIG. 16 illustrates an embodiment for determining a plan for ablation.

FIG. 16 illustrates the apparatus of an embodiment for selecting a plan for ablating a target tissue 203. The method is advantageous for ablating large tissues that require several ablations, but it also functions for target tissues only requiring a single ablation. FIG. 16 illustrates a bone drill positioned with its tip at the distal boundary of a target tissue 203. The proximal portion of bone drill shaft 134 includes plan selection markings 262 which include markings PM1 to PM15. In the example of FIG. 16, PM1 is aligned with a cooperating feature of the cannula. A larger target tissue would have resulted in a higher plan selection marking aligning with the cooperating feature of the cannula. While the embodiment of FIG. 16 has 15 plan selection markings 262, alternative embodiments have more or fewer markings. An example follows.

Example

An ablation target has a length of 16 mm. Probe A has a ablation length of 5 mm, probe B has an ablation length of 6 mm, and probe C has an ablation length of 10 mm. When using the apparatus of FIG. 16, PM2 for plan number two is indicated. Plan number two includes the following options for probe selection for tip-to-tail placement:
Create lesion with exact dimension of ablation target: Probe C+Probe B (for 16 mm lesion)
Create lesion smaller than ablation target: Probe A+Probe C (for 15 mm lesion)
Create lesion larger than ablation target: Probe B+Probe B+Probe B (for 18 mm lesion)

When using this method, the physician does not need to determine which combination of probes should be used in a given situation. The probe combinations have been previously optimized and are provided to the physician in a look-up chart. As understood by those who are skilled in the art, this method can be extended to map lesions radially, or both radially and axially simultaneously.

Thus, as described herein above, a method for treating tissue includes an intra-operative mapping of a probe ablation zone. The method uses a system that maps the proximal and distal margins of the probe ablation zone using tools to access the ablation target. In some embodiments the tools comprise a bone drill, and an introducer assembly including a cannula and a stylet.

An additional method for treating tissue includes intra-operative probe selection for ablation. The method comprises mapping a proximal margin and a distal margin of a probe ablation zone using tools with features or markings that cooperate to indicate which probe to use to achieve a desired ablation volume. In some embodiments, the method includes the mapping of at least two locations. The method further facilitates probe placement for delivering energy to treat (ablate) a desired ablation volume of a target tissue by mapping both the target tissue as well as possible probe ablation zones.

Examples

1. A method for intra-operative mapping of a probe ablation zone, the method comprising accessing a treatment site using one or more treatment access tools, and defining a proximal margin and a distal margin of a probe ablation zone using the one or more treatment access tools.
2. The method of example 1, the one or more treatment access tools comprising an introducer assembly including a cannula and a stylet positioned therein, wherein accessing the treatment site comprises advancing the introducer assembly to a proximal edge of a desired ablation volume.
3. The method of example 2, wherein the proximal margin of the probe ablation zone is mapped by visualizing a distal tip of the introducer assembly positioned at the proximal edge of the desired ablation volume.
4. The method of example 2, wherein the proximal margin of the probe ablation zone is mapped by visualizing a distal tip of the cannula positioned at the proximal edge of the desired ablation volume.
5. The method of example 3, further comprising withdrawing the stylet from the cannula and inserting a medical instrument into the cannula.
6. The method of example 5, wherein the treatment site includes bone tissue and wherein the medical instrument is a bone drill for accessing bone tissue at the treatment site.
7. The method of example 5, wherein the treatment site includes soft tissue and wherein the medical instrument is a needle for piercing tissue at the treatment site.
8. The method of example 5, the medical instrument including a marking located so as to indicate that a distal end of the medical instrument is aligned with a distal end of the cannula when the marking is aligned with a cooperating feature of the cannula, the method further comprising advancing the medical instrument through the cannula until the marking is aligned with the cooperating feature of the cannula.
9. The method of example 8, the medical instrument comprising one or more indicia located proximal of the marking, the method further comprising defining a distal margin of the probe ablation zone by advancing the medical instrument and aligning one of the one or more indicia with the cooperating feature of the cannula, whereby the position of the distal end of the medical instrument defines the distal margin of the probe ablation zone.
10. The method of example 9, further comprising mapping the distal margin of the probe ablation zone by visualizing the distal tip of the medical instrument.
11. The method of any one of examples 1 to 10, wherein fluoroscopic imaging is used for visualizing.
12. The method of any one of examples 1 to 10, wherein visualization is accomplished using an imaging modality selected from the group consisting of X-ray imaging and computed tomography (CT).
13. The method of example 10, further comprising selecting a probe for ablating tissue at the treatment site based upon which of the one or more indicia is aligned with the cooperating feature of the cannula.
14. The method of example 13, further comprising withdrawing the medical instrument from the cannula, inserting the probe into the cannula, and delivering energy to ablate the tissue at the treatment site.
15. A system for treating tissue, the system comprising:
an introducer assembly comprising a cannula, the cannula defining a lumen;
a medical instrument for accessing tissue at a treatment site through the lumen of the cannula, the medical instrument defining one or more indicia, each indicia for defining a probe ablation zone; and
one or more probes, each probe corresponding to a single indicia of the medical instrument, each probe operable to ablate tissue within a respective probe ablation zone.
16. The system of example 15, wherein the introducer assembly defines a trocar tip.
17. The system of example 15, wherein the medical instrument is a bone drill.
18. The system of example 15, wherein the medical instrument is a needle for piercing tissue.
19. The system of example 15, wherein the medical instrument defines a marking located so as to indicate that a distal end of the medical instrument is aligned with a distal end of the cannula when the medical instrument is inserted through the cannula such that the marking is aligned with a cooperating feature of the cannula.
20. The system of example 15, wherein the indicia are color coded.
21. The system of example 15, the one or more indicia comprising at least two indicia longitudinally spaced apart from one another on the medical instrument.
22. The system of example 15, wherein the one or more indicia are located along the medical instrument such that, when one of the one or more indicia is aligned with a cooperating feature of the cannula when the medical instrument is inserted through the cannula, a distance by which a distal end of the medical instrument extends beyond a distal end of the cannula is substantially equivalent to a length of the probe ablation zone operable to be ablated by the probe having the feature corresponding to the one of the one or more indicia.

23. The system of example 15, further comprising an imaging system.

24. The system of example 23, wherein the imaging system is a fluoroscopic imaging system.

25. The system of example 23, wherein the imaging system is a computed tomography (CT) imaging system.

26. The system of example 15, wherein each of the probes is operable to deliver electrical energy in a bipolar manner.

27. The system of example 15, wherein each of the probes has a different respective active tip size.

28. The system of example 15, further comprising a generator for supplying electrical energy to any of the probes connected thereto.

29. The system of example 28, wherein the generator is operable to supply energy at about 1 watt to about 100 watts.

30. The system of example 28, wherein the generator is operable to supply energy at about 1 watt to about 50 watts.

31. The system of example 28, wherein the generator is operable to supply energy at greater than about 100 watts.

32. A method for intra-operative probe selection for ablation of tissue at a treatment site, the method comprising mapping a proximal margin and a distal margin of a probe ablation zone at the treatment site using tools having features that cooperate to determine probe selection for achieving a desired ablation defined by the probe ablation zone.

33. The method of example 32, wherein the tools comprise an introducer assembly including a cannula and a stylet positioned therewithin, the method comprising advancing the introducer assembly and positioning the introducer assembly at a first location at the treatment site such that a distal tip of the introducer assembly defines the proximal margin of the probe ablation zone.

34. The method of example 33, wherein the tools further comprise a medical instrument selected from the group consisting of a bone drill and a needle, and wherein the method further comprises withdrawing the stylet from the cannula and inserting the medical instrument into the cannula.

35. The method of example 34, further comprising advancing the medical instrument through the cannula and observing a marking on the medical instrument which cooperates with a cooperating feature of the cannula to indicate when a distal end of the medical instrument is aligned with a distal end of the cannula.

36. The method of example 35, the medical instrument comprising one or more indicia located proximal of the marking, the method further comprising advancing the medical instrument through the cannula, observing the indicia and aligning one of the indicia with the cooperating feature of the cannula in order to define a distal margin of the probe ablation zone at a location of the distal end of the medical instrument.

37. The method of example 36, further comprising selecting a probe operable to ablate tissue between the proximal and distal margins of the probe ablation zone based on the indicia aligned with the cooperating feature of the cannula.

38. The method of example 36, wherein at least two indicia are longitudinally displaced along the medical instrument.

39. The method of example 36, wherein the indicia are color coded.

40. The method of example 39, wherein each of the indicia has a color code which corresponds with a color coding associated with the selected probe.

41. The method of example 35, wherein the cooperating feature of the cannula is a cannula marking.

42. The method of example 35, wherein the cooperating feature of the cannula is a proximal end of the cannula.

43. The method of example 37, further comprising withdrawing the medical instrument, inserting the probe into the cannula and advancing the probe to the first location.

44. The method of example 43, wherein the probe is advanced until it is limited from further advancement through the cannula.

45. The method of example 43, further comprising supplying energy to the probe for ablating tissue, including at least a portion of a target tissue, at the first location.

46. The method of example 45, wherein a temperature at the probe during ablation ranges from about 40° C. to about 100° C.

47. The method of example 45, wherein a temperature at the probe during ablation ranges from about 65° C. to about 70° C.

48. The method of example 45, wherein a temperature at the probe during ablation is about 100° C.

49. The method of example 45, wherein a temperature at the probe during ablation is about 90° C.

50. The method of example 45, wherein a temperature at the probe during ablation is about 70° C.

51. The method of example 45, wherein energy is delivered from the probe for a period of time ranging from about 6.5 minutes to about 15 minutes.

52. The method of example 45, wherein energy is delivered from the probe for a period of time of about 6.5 minutes.

53. The method of example 45, wherein energy is delivered from the probe for a period of time of about 7.5 minutes.

54. The method of example 45, wherein energy is delivered from the probe for a period of time of about 15 minutes.

55. The method of any one of examples 32 to 54, further comprising visualization of one or more of the tools using an imaging system selected from the group consisting of X-ray imaging, fluoroscopic imaging, and Computed Tomography (CT).

56. The method of example 45, wherein at least a portion of the ablation zone is within or surrounded by bone tissue.

57. The method of example 56, wherein the bone tissue comprises a vertebra.

58. The method of example 45, further comprising withdrawing the probe from the cannula and inserting the stylet into the cannula after ablating at the first location.

59. The method of example 58, further comprising advancing the introducer assembly to the distal margin of the probe ablation zone of the first location to thereby define a probe ablation zone proximal margin at a second location, and mapping the probe ablation zone proximal margin at the second location by visualizing the distal tip of the introducer assembly.

60. The method of example 59, further comprising: withdrawing the stylet from the cannula and inserting the medical instrument into the cannula; defining a distal margin of the probe ablation zone at the second location by advancing the medical instrument and aligning one of the one or more indicia with the cooperating feature of the cannula, whereby the position of the distal end of the medical instrument defines the distal margin of the probe ablation zone at the second location; and mapping the distal margin of the probe ablation zone at the second location by visualizing the distal tip of the medical instrument.

61. The method of example 60, further comprising imaging a remaining portion of the target tissue.

62. The method of example 61, wherein the distal tip of the medical instrument is positioned distal of a distal edge of a desired ablation volume at the second location.

63. The method of example 62, further comprising confirming that the tissue within the probe ablation zone at the second location is acceptable for ablation.

64. The method of example 63, further comprising:
selecting a corresponding probe operable to ablate tissue between the proximal and distal margins of the probe ablation zone at the second location based on the indicia aligned with the corresponding feature of the cannula;
withdrawing the medical instrument and inserting the corresponding probe into the cannula; and
advancing the corresponding probe to a position for ablating tissue within the probe ablation zone at the second location.

65. The method of example 64, further comprising delivering energy to ablate a quantity of the tissue within the probe ablation zone at the second location.

66. The method of example 62, further comprising withdrawing the cannula and medical instrument until the distal tip of the medical instrument is positioned at the distal edge of the desired ablation volume at the second location while retaining alignment between the one of the one or more indicia of the medical instrument with the cooperating feature of the cannula.

67. The method of example 66, further comprising:
selecting a corresponding probe based on the one of the one or more indicia aligned with the corresponding feature of the cannula;
withdrawing the medical instrument;
inserting the probe into the cannula; and
advancing the probe to a position for ablating tissue within the probe ablation zone at the second location.

68. The method of example 67, further comprising delivering energy to ablate a quantity of the tissue within the probe ablation zone at the second location.

69. The method of example 62, further comprising withdrawing the cannula while maintaining the position of the distal tip of the medical instrument distal to the distal edge of the desired ablation volume at the second location while the tip of the cannula is positioned proximal of a proximal edge of the desired ablation volume at the second location to define the proximal margin of the probe ablation zone at the second location.

70. The method of example 69, wherein the desired ablation volume at the second location is centered within the probe ablation zone.

71. The method of example 69, further comprising:
selecting a corresponding probe operable to ablate tissue between the proximal and distal margins of the probe ablation zone at the second location based on the one of the one or more indicia aligned with the corresponding feature of the cannula;
withdrawing the medical instrument;
inserting the probe into the cannula; and
advancing the probe to a position for ablating tissue within the probe ablation zone at the second location.

72. The method of example 71, further comprising delivering energy to ablate a quantity of the tissue within the probe ablation zone at the second location.

73. The method of example 59, further comprising:
withdrawing the stylet from the cannula and inserting the medical instrument into the cannula;
defining a first distal margin of the probe ablation zone at the second location by advancing the medical instrument and aligning one of the one or more indicia with the cooperating feature of the cannula, whereby the position of the distal end of the medical instrument defines the first distal margin of the probe ablation zone at the second location; and
mapping the first distal margin of the probe ablation zone at the second location by visualizing the distal tip of the medical instrument.

74. The method of example 73, further comprising:
defining a second distal margin of the probe ablation zone at the second location by further advancing the medical instrument and aligning a second of the one or more indicia with the cooperating feature of the cannula, whereby the position of the distal end of the medical instrument defines the second distal margin of the probe ablation zone at the second location; and
mapping the second distal margin of the probe ablation zone at the second location by visualizing the distal tip of the medical instrument.

75. The method of example 74, further comprising mapping a desired ablation volume at the second location by visualizing a portion of target tissue distal to the probe ablation zone of the first location.

76. The method of example 75, further comprising:
determining a first distance defined by the distance between the proximal margin of the probe ablation zone at the second location and the first distal margin of the probe ablation zone at the second location wherein the first distance is a length of a probe ablation zone of a first probe;
determining a second distance defined by the distance between the proximal margin of the probe ablation zone at the second location and the second distal margin of the probe ablation zone at the second location wherein the second distance is a length of a probe ablation zone of a second probe;
comparing the first distance and the second distance to a third distance defined by a length of the desired ablation volume at the second location and determining whether the length of the probe ablation zone of the first probe or the length of the probe ablation zone of the second probe is desired for ablating at the second location; and
selecting a probe from the first probe and the second probe for at least one delivery of energy.

77. The method of example 76, the method further comprising:
withdrawing the medical instrument;
inserting the selected probe into the cannula;

advancing the selected probe to a position for ablating tissue; and supplying energy to the selected probe for ablating tissue, including at least a portion of the target tissue, at the second location.

78. The method of example 77, wherein the distal margin of the probe ablation zone at the second location is within the desired ablation volume, the method further comprising:
mapping a probe ablation zone at a third location for the selected probe, wherein a distal margin of the probe ablation zone at the third location is equivalent to a distal edge of the desired ablation volume;
wherein the probe ablation zone at the second location and the probe ablation zone at the third location are longitudinally aligned and overlapping.

79. The method of example 77, wherein the distal margin of the probe ablation zone at the second location is within the desired ablation volume, the method further comprising:
mapping a probe ablation zone at a third location for the selected probe, wherein a distal margin of the probe ablation zone at the third location is proximal of a distal edge of the desired ablation volume;
wherein the probe ablation zone at the second location and the probe ablation zone at the third location are longitudinally aligned and positioned end-to-end.

80. The method of example 76, the method further comprising confirming that tissue within the probe ablation zone of the selected probe at the second location is acceptable for ablation.

81. The method of examples 78 or 79, further comprising confirming that tissue within the probe ablation zone of the selected probe at the third location is acceptable for ablation.

82. The method of example 81, further comprising: withdrawing the medical instrument; inserting the selected probe into the cannula; advancing the selected probe to a position for ablating tissue; and supplying energy to the selected probe and ablating tissue.

83. The method of examples 1 or 32, further comprising saving a screen image as a stored image whereby the stored image may be viewed at a later time.

84. The method of examples 1 or 32, wherein an imaging system includes at least two viewing screens and wherein the method further comprises viewing a screen image using at least one of the at least two viewing screens.

85. The method of example 84, further comprising transferring the screen image from a first viewing screen to a second viewing screen.

86. The system of example 20, wherein each of the indicia has an indicium color code which corresponds with a probe color code of one of the one or more probes.

87. The system of example 86, further comprising a respective packaging for each of the one or more probes, each respective packaging indicating a packaging color code corresponding to the color code associated with the one or more probes associated with the respective packaging.

88. The system of example 19, wherein the cooperating feature of the cannula is a slot.

89. The system of example 19, wherein the cooperating feature of the cannula is an aperture.

90. The system of example 19, wherein the cooperating feature of the cannula is a cannula marking.

91. The system of example 19, wherein the cooperating feature of the cannula is a proximal end of the cannula.

92. The system of example 91, the cannula including a handle, and a hub projecting proximally from the handle, wherein the handle and hub define a longitudinal portion of the lumen, and wherein the hub defines the proximal end of the cannula.

93. The system of example 26, wherein each of the probes is operable to deliver electrical energy in a radiofrequency range.

94. The system of example 28, the generator comprising a temperature look-up table for storing one or more operating temperatures of the one or more probes.

95. The system of example 94, wherein each indicium corresponds with one of the one or more operating temperatures.

96. The system of example 94, wherein each of the indicia is color coded and each of the operating temperatures is color coded with a corresponding color code.

97. The system of example 94, the generator being operable to detect a probe of the one or more probes connected thereto and to select a corresponding one of the one or more operating temperatures from the temperature look-up table.

98. The system of example 28, further comprising at least two color coded generator switches for selecting probe operating temperatures wherein each color coded switch corresponds with a color code of a respective probe.

99. A method of ablating a target tissue, comprising the steps of:
positioning an introducer assembly, including a cannula and a stylet positioned therethrough, within a target tissue, thereby defining a proximal margin of a probe ablation zone;
imaging the proximal margin of the probe ablation zone to thereby map the proximal margin;
removing the stylet from the cannula;
inserting a bone drill into the cannula; and
advancing the bone drill until a distal tip of the bone drill is at a distal edge of a desired ablation volume, the distal tip thereby defining a distal margin of a probe ablation zone.

100. The method of example 99, further comprising:
withdrawing the cannula a until an indicium associated with the bone drill aligns with a corresponding feature of the cannula while maintaining a position of the bone drill; and
visualizing the distal tip of the bone drill to thereby map the distal margin of the probe ablation zone.

101. The method of example 100, further comprising:
removing the bone drill from the cannula;
inserting a probe corresponding to the indicium into the cannula and advancing it until it is at an ablation position of the probe; and
delivering energy through the probe to form a lesion corresponding to the probe ablation zone.

102. The method of example 101, further comprising:
withdrawing the probe from the cannula;
re-inserting the bone drill into the cannula; and
advancing the bone drill until it protrudes from a distal end of the cannula, a distal tip of the bone drill is at the proximal margin of the probe ablation zone, and the tip of the bone drill also defines a distal edge of a next desired ablation volume and a distal margin of the next probe ablation zone.

103. The method of example 102, further comprising maintaining the position of the bone drill while withdrawing the cannula a distance until one of the one or more indicia lines up with the corresponding feature at which time the distal tip of the bone drill still defines a distal edge of the next desired ablation volume.
104. The system of example 86, wherein the probe color code is located on a hub of the one of the one or more probes.
105. The method of example 36, further comprising imaging a target tissue at the first location.
106. The method of example 105, wherein the distal end of the medical instrument is positioned distal of a distal edge of a desired ablation volume at the first location.
107. The method of example 106, further comprising confirming that the tissue within the probe ablation zone at the first location is acceptable for ablation.
108. The method of example 107, further comprising:
selecting a corresponding probe operable to ablate tissue between the proximal and distal margins of the probe ablation zone based on the indicia aligned with the corresponding feature of the cannula;
withdrawing the medical instrument and inserting the corresponding probe into the cannula; and
advancing the corresponding probe to a position for ablating tissue within the probe ablation zone.
109. The method of example 108, further comprising delivering energy to ablate a quantity of the tissue within the probe ablation zone.
110. The method of example 106, further comprising withdrawing the cannula and medical instrument until the distal end of the medical instrument is positioned at the distal edge of the desired ablation volume at the first location while retaining alignment between the one of the indicia of the medical instrument with the cooperating feature of the cannula.
111. The method of example 110, further comprising:
selecting a corresponding probe based on the one of the indicia aligned with the corresponding feature of the cannula;
withdrawing the medical instrument;
inserting the probe into the cannula; and
advancing the probe to a position for ablating tissue within the probe ablation zone.
112. The method of example 111, further comprising delivering energy to ablate a quantity of the tissue within the probe ablation zone.
113. The method of example 106, further comprising withdrawing the cannula while maintaining the position of the distal end of the medical instrument distal to the distal edge of the desired ablation volume at the first location while the tip of the cannula is positioned proximal of a proximal edge of the desired ablation volume at the first location to define the proximal margin of the probe ablation zone at the first location.
114. The method of example 113, wherein the desired ablation volume is centered within the probe ablation zone at the first location.
115. The method of example 114, further comprising:
selecting a corresponding probe operable to ablate tissue between the proximal and distal margins of the probe ablation zone at the first location based on the one of the indicia aligned with the corresponding feature of the cannula;
withdrawing the medical instrument;
inserting the corresponding probe into the cannula; and
advancing the probe to a position for ablating tissue within the probe ablation zone at the first location.
116. The method of example 115, further comprising delivering energy to ablate a quantity of the tissue within the probe ablation zone.
117. The system of example 15, further comprising a measuring instrument operable to be coupled to a proximal portion of the medical instrument for marking distances perpendicular to a longitudinal axis of the medical instrument.
118. The method of example 35, the medical instrument comprising one or more indicia, the method further comprising:
defining a first distal margin corresponding to a first probe ablation zone by advancing the medical instrument and aligning a first of the one or more indicia with the cooperating feature of the cannula, the first distal margin being defined by the distal end of the medical instrument; and
mapping the first distal margin by visualizing the distal end of the medical instrument.
119. The method of example 118, further comprising:
defining a second distal margin corresponding to a second probe ablation zone by further advancing the medical instrument and aligning a second of the one or more indicia with the cooperating feature of the cannula, whereby the position of the distal end of the medical instrument defines the second distal margin; and
mapping the second distal margin by visualizing the distal tip of the medical instrument.
120. The method of example 119, further comprising mapping a desired ablation volume by visualizing a target tissue.
121. The method of example 120, the method further comprising:
selecting a probe for at least one delivery of energy based on one of the one or more indicia.
122. The method of example 121, the method further comprising:
withdrawing the medical instrument;
inserting the selected probe into the cannula;
advancing the selected probe to a position for ablating tissue; and
supplying energy to the selected probe for ablating tissue, including at least a portion of the target tissue.
123. The system of example 15, further comprising an imaging tool, the imaging tool comprising:
a collar having a center hole for receiving a shaft of the medical instrument;
a first extending member extending outwardly from the collar; and
at least one first member visualization element associated with the first extending member.
124. The system of example 123, wherein the imaging tool further comprises a second extending member extending outwardly from the collar in a direction opposite to the first extending member.
125. The system of example 124, wherein the second extending member comprises at least one second member visualization element and wherein one of the at least one first member visualization elements and one of the at least one second member visualization elements are equidistant from the collar and define a first pair of visualization elements.
126. The system of example 125, wherein the first pair of visualization elements are operable to be visualized using an imaging system to thereby define opposite side radial margins of a first probe ablation zone when the imaging tool is coupled to the medical instrument.

127. The system of example 126, wherein the first pair of visualization elements defines a first imaging tool indicator corresponding to a first probe of the one or more probes.

128. The system of example 127, further comprising a second pair of visualization elements comprising a second of the at least one first member visualization elements and a second of the at least one second member visualization elements.

129. The system of example 128, wherein the second pair of visualization elements is operable to be visualized using the imaging system to thereby define opposite side radial margins of a second probe ablation zone when the imaging tool is coupled to the medical instrument.

130. The system of example 129, wherein the second pair of visualization elements defines a second imaging tool indicator corresponding with a second probe of the one or more probes.

131. A method for mapping side-by-side probe ablation zones, the method comprising:
positioning a medical instrument coupled to an imaging tool, as described in any one of examples 123-130, at a target site;
defining a first lateral probe ablation zone of a probe at a first position by visualizing a pair of visualization elements of the imaging tool;
repositioning the medical instrument laterally; and
defining a second lateral probe ablation zone of the probe at a second position.

132. The method of example 131, wherein the first lateral probe ablation zone and the second lateral probe ablation zone are substantially adjacent one another.

133. The method of example 131, wherein the first lateral probe ablation zone and the second lateral probe ablation zone are at least partially overlapping one another.

134. A method for intra-operative mapping of a probe ablation zone, the method comprising:
accessing a treatment site using one or more treatment access tools and defining a proximal margin and a distal margin of a probe ablation zone using the one or more treatment access tools, the probe ablation zone being substantially equivalent to a target tissue being targeted for ablation; and
selecting a probe using the one or more treatment access tools, the probe being operable to ablate a region of tissue larger than the probe ablation zone.

135. The method of example 134, further comprising adjusting a power setting of an energy system providing power to the probe to provide an expanded margin of ablation around the target tissue.

136. A method for intra-operative probe selection for ablation of tissue at a treatment site, the method comprising mapping a proximal margin and a distal margin of a probe ablation zone at the treatment site using access tools having features that cooperate to determine probe selection from a group of probes for achieving a desired ablation defined by the probe ablation zone.

137. A method for intra-operative selection of a probe temperature for ablation of tissue at a treatment site, the method comprising mapping a target tissue at a treatment site using an imaging system to define a probe ablation zone, and using access tools having features that cooperate to determine, for a particular probe, a pre-defined probe temperature for achieving a desired ablation defined by the probe ablation zone.

138. The method of example 137, wherein the access tools comprise an introducer assembly including a cannula.

139. The method of example 138, wherein the access tools further comprise a medical instrument selected from the group consisting of a bone drill and a needle.

140. The method of example 139, further comprising advancing the medical instrument through the cannula until it advances to a distal boundary of the probe ablation zone and visualizing a temperature selection marking on the medical instrument which aligns with a cooperating feature of the cannula to select the pre-defined probe temperature.

141. A method for intra-operative selection of a treatment plan to ablate a target tissue requiring one or more ablations, the method comprising mapping a target tissue at a treatment site using an imaging system to define a probe ablation zone and using access tools having cooperating features to determine a treatment plan for achieving a desired ablation defined by the probe ablation zone.

142. The method of example 141, wherein the access tools comprise an introducer assembly including a cannula.

143. The method of example 142, wherein the access tools further comprise a medical instrument selected from the group consisting of a bone drill and a needle.

144. The method of example 143, further comprising advancing the medical instrument through the cannula until it advances to a distal boundary of the probe ablation zone and visualizing a plan selection marking on the medical instrument which aligns with a cooperating feature of the cannula to indicate the treatment plan for ablating the target tissue.

145. The method of example 144, further comprising referencing a data storage system using the plan selection marking to select at least one probe, from a plurality of probes, to effect the treatment plan.

146. The system of example 117, the measuring instrument comprising a plurality of measurement indicia.

147. A system for treating tissue, the system comprising:
an introducer assembly comprising a cannula and a stylet, the cannula defining a lumen;
a plurality of medical instruments for accessing tissue at a treatment site through the lumen of the cannula, each medical instrument defining one or more indicia, each indicium for defining a probe ablation zone; and
one or more probes, each probe corresponding to a single indicium of the medical instrument, each probe operable to ablate tissue within a respective probe ablation zone.

148. The system of example 147, wherein the stylet comprises a plurality of stylet indicia.

149. The system of example 147, wherein each of the plurality of stylet indicia corresponds to a respective one of the plurality of medical instruments.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A method for intra-operative mapping of a probe ablation zone, the method comprising:
   inserting portions of an introducer assembly into a human body, the introducer assembly including a cannula and a stylet, each of the cannula and the stylet having a proximal end and an opposite distal end, the cannula including a lumen extending between the proximal end and the distal end thereof, and the stylet being received within the lumen of the cannula during the inserting of the portions of the introducer assembly into the human body;
   visualizing the position of the introducer assembly during the inserting of the portions of the introducer assembly into the human body;
   accessing a treatment site encompassing a tumor using the introducer assembly, the treatment site being larger than the tumor, the tumor being located within the treatment site, and soft tissue and/or bone of the treatment site being exclusive of the tumor;
   positioning the distal ends of the cannula and the stylet at least adjacent a proximal portion of the treatment site to define a proximal margin of the probe ablation zone;
   removing the stylet from the lumen of the cannula and inserting portions of a drill through the cannula and into the human body, the drill including a proximal end and an opposite distal end;
   visualizing the position of the drill at least during the inserting of the drill into the human body;
   positioning the distal end of the drill across a portion of the treatment site, across a portion of the tumor, and beyond a distal portion of the tumor to a distal end of the treatment site to define a distal margin of the probe ablation zone;
   mapping the distal margin of the probe ablation zone by visualizing the distal end of the drill; and
   mapping the probe ablation zone using the proximal margin and the distal margin thereof to define longitudinal boundaries of the probe ablation zone.

2. The method of claim 1, wherein the proximal margin of the probe ablation zone is mapped by visualizing the distal end of at least one of the cannula and the stylet positioned at the proximal edge of the probe ablation zone.

3. The method of claim 1, wherein the proximal margin of the probe ablation zone is mapped by visualizing the distal end of the cannula positioned at the proximal edge of the probe ablation zone.

4. The method of claim 1, wherein the drill includes a marking located so as to indicate that the distal end of the drill is aligned with the distal end of the cannula when the marking is aligned with a cooperating feature of the cannula, the method further comprising advancing the drill through the cannula until the marking is aligned with the cooperating feature of the cannula.

5. The method of claim 4, wherein the drill comprises one or more indicia located proximal of the marking, the method further comprising defining the distal margin of the probe ablation zone by advancing the drill and aligning one of the one or more indicia with the cooperating feature of the cannula, whereby the position of the distal end of the drill defines the distal margin of the probe ablation zone.

6. The method of claim 5, further comprising selecting a probe for ablating the ablation zone based upon which of the one or more indicia is aligned with the cooperating feature of the cannula.

7. The method of claim 6, further comprising withdrawing the drill from the cannula, inserting the probe into the cannula, and delivering energy to ablate the ablation zone.

8. The method of claim 1, wherein fluoroscopic imaging is used for visualizing.

9. The method of claim 1, wherein visualization is accomplished using an imaging modality selected from the group consisting of X-ray imaging and computed tomography (CT).

10. The method of claim 1, further comprising saving a screen image of a mapped ablation zone as a stored image whereby the stored image may be viewed at a later time.

11. The method of claim 1, wherein an imaging system includes at least two viewing screens and wherein the method further comprises viewing a screen image of a mapped ablation zone using at least one of the at least two viewing screens.

12. The method of claim 11, further comprising transferring the screen image from a first viewing screen to a second viewing screen.

13. A method for intra-operative mapping of a probe ablation zone, the method comprising:
   inserting portions of a cannula into a human body, the cannula having a proximal end, an opposite distal end, and a lumen extending between the proximal end and the distal end;
   visualizing the position of the cannula during the inserting of the portions of the cannula into the human body;
   accessing a treatment site encompassing acted area tumor using the cannula, the treatment site being larger than the tumor, the tumor being located within the treatment site, and soft tissue and/or bone of the treatment site being exclusive of the tumor;
   positioning the distal end of the cannula at least adjacent a proximal portion of the treatment site to define a proximal margin of the probe ablation zone;
   inserting portions of a drill through the cannula into the human body, the drill including a proximal end and an opposite distal end;
   visualizing the position of the drill at least during the inserting of the drill into the human body;
   positioning the distal end of the drill across a portion of the treatment site, across a portion of the tumor, and beyond a distal portion of the tumor to a distal end of the treatment site to define a distal margin of the probe ablation zone;
   mapping the distal margin of the probe ablation zone by visualizing the distal end of the drill;
   mapping the probe ablation zone using the proximal margin and the distal margin, the probe ablation zone being substantially equivalent to the treatment site; and selecting a probe sized to ablate a region of tissue larger than the probe ablation zone.

14. The method of claim 13, further comprising adjusting a power setting of an energy system providing power to the probe to provide an expanded margin of ablation around the treatment site.

15. The method of claim 13, wherein the proximal margin of the probe ablation zone is mapped by visualizing the distal end of the cannula positioned at a proximal edge of the probe ablation zone.

16. The method of claim 13, wherein the drill includes a marking located so as to indicate that the distal end of the drill is aligned with the distal end of the cannula when the marking is aligned with a cooperating feature of the cannula, the method further comprising advancing the drill through the cannula until the marking is aligned with the cooperating feature of the cannula.

17. The method of claim 16, wherein the drill comprises one or more indicia located proximal of the marking, the method further comprising defining the distal margin of the probe ablation zone by advancing the drill and aligning one of the one or more indicia with the cooperating feature of the cannula, whereby the position of the distal end of the drill defines the distal margin of the probe ablation zone.

18. A method for intra-operative mapping of a probe ablation zone, the method comprising:
- inserting portions of a cannula into a human body, the cannula having a proximal end, an opposite distal end, and a lumen extending between the proximal end and the distal end;
- accessing a treatment site encompassing a tumor using the cannula, the treatment site being larger than the tumor, the tumor being located within the treatment site, and soft tissue and/or bone of the treatment site being exclusive of the tumor;
- positioning the distal end of the cannula at least adjacent a proximal portion of the treatment site to define a proximal margin of the probe ablation zone;
- mapping the proximal margin of the probe ablation zone by visualizing the distal end of the cannula;
- inserting portions of a drill through the cannula into the human body, the drill including a proximal end and an opposite distal end;
- positioning the distal end of the drill across a portion of the treatment site, across a portion of the tumor, and beyond a distal portion of the tumor to a distal end of the treatment site to define a distal margin of the probe ablation zone;
- mapping the distal margin of the probe ablation zone by visualizing the distal end of the drill;
- mapping the probe ablation zone using the proximal margin and the distal margin, the probe ablation zone being substantially equivalent to the treatment site; and
- selecting a probe sized to ablate a region of tissue larger than the probe ablation zone.

19. The method of claim 18, wherein the drill includes a marking located so as to indicate that the distal end of the drill is aligned with the distal end of the cannula when the marking is aligned with a cooperating feature of the cannula, the method further comprising advancing the drill through the cannula until the marking is aligned with the cooperating feature of the cannula.

20. The method of claim 19, wherein the drill comprises one or more indicia located proximal of the marking, the method further comprising defining the distal margin of the probe ablation zone by advancing the drill and aligning one of the one or more indicia with the cooperating feature of the cannula, whereby the position of the distal end of the drill defines the distal margin of the probe ablation zone.

* * * * *